US007328059B2

(12) United States Patent
Sevick-Muraca et al.

(10) Patent No.: US 7,328,059 B2
(45) Date of Patent: Feb. 5, 2008

(54) IMAGING OF LIGHT SCATTERING TISSUES WITH FLUORESCENT CONTRAST AGENTS

(75) Inventors: Eva Sevick-Muraca, Lafayette, IN (US); Tamara L. Troy, Chandler, AZ (US); Jeffery S. Reynolds, Granger, IN (US)

(73) Assignee: The Texas A & M University System, College Station, TX (US)

( * ) Notice: Subject to any disclaimer, the term of this patent is extended or adjusted under 35 U.S.C. 154(b) by 1260 days.

(21) Appl. No.: 09/870,144

(22) Filed: May 30, 2001

(65) Prior Publication Data

US 2002/0072677 A1 Jun. 13, 2002

Related U.S. Application Data

(63) Continuation of application No. 09/367,148, filed as application No. PCT/US98/02354 on Feb. 6, 1998, now abandoned, and a continuation-in-part of application No. 08/702,060, filed on Aug. 23, 1996, now Pat. No. 5,865,754.

(60) Provisional application No. 60/039,318, filed on Feb. 7, 1997.

(51) Int. Cl.
*A61B 6/00* (2006.01)
(52) U.S. Cl. .................. 600/473; 600/431; 600/476
(58) Field of Classification Search .............. 600/431, 600/476, 473, 310, 477, 407; 356/317, 318; 128/899; 382/133, 191; 250/454.1
See application file for complete search history.

(56) References Cited

U.S. PATENT DOCUMENTS 4,541,438 A 9/1985 Parker et al. ............... 128/664

(Continued)

FOREIGN PATENT DOCUMENTS

EP 0 959 341 A1 11/1999

(Continued)

OTHER PUBLICATIONS

E. M. Sevick et al., "*Localization of absorber in Scattering Media by use of frequency-domain measurements of time-dependent photon migration*", Applied Optics, vol. 33 No. 16, Jun. 1994, pp. 3562-3570.

(Continued)

*Primary Examiner*—Eleni M. Mantis Mercader
*Assistant Examiner*—Baisakhi Roy
(74) *Attorney, Agent, or Firm*—Baker Botts L.L.P.

(57) ABSTRACT

A system and method for non-invasive biomedical optical imaging and spectroscopy with low-level light is described. The technique includes a modulated light source coupled to tissue to introduce excitation light. Fluorescent light emitted in response to the excitation light is detected with a sensor. The AC intensity and phase of the excitation and detected fluorescent light is provided to a processor operatively coupled to the sensor. A processor employs the measured emission kinetics of excitation and fluorescent light to "map" the spatial variation of one or more fluorescence characteristics of the tissue and generate a corresponding image of the tissue via an output device. The fluorescence characteristic may be provided by exogenous contrast agents, endogenous fluorophores, or both. A technique to select or design an exogenous fluorescent contrast agent to improve image contrast is also disclosed.

16 Claims, 26 Drawing Sheets

U.S. PATENT DOCUMENTS

| | | | |
|---|---|---|---|
| 5,022,757 A | 6/1991 | Modell | 128/664 |
| 5,119,815 A | 6/1992 | Chance | 128/633 |
| 5,142,372 A | 8/1992 | Alfano et al. | 128/664 |
| 5,190,729 A | 3/1993 | Hauenstein et al. | |
| 5,208,651 A | 5/1993 | Buican | 356/346 |
| 5,213,105 A | 5/1993 | Gratton et al. | 128/664 |
| 5,340,991 A | 8/1994 | Fransen et al. | 128/664 |
| 5,353,799 A | 10/1994 | Chance | 128/664 |
| 5,413,098 A | 5/1995 | Benaron | 128/633 |
| 5,421,337 A | 6/1995 | Richards-Kortum et al. | 128/633 |
| 5,421,339 A | 6/1995 | Ramanujam et al. | 128/665 |
| 5,424,843 A | 6/1995 | Tromberg et al. | 356/442 |
| 5,441,054 A | 8/1995 | Tsuchiya | 128/665 |
| 5,452,723 A | 9/1995 | Wu et al. | 128/665 |
| 5,485,530 A * | 1/1996 | Lakowicz et al. | 382/191 |
| 5,504,337 A | 4/1996 | Lakowicz et al. | 250/461.2 |
| 5,507,287 A | 4/1996 | Palcic et al. | 128/633 |
| 5,579,773 A | 12/1996 | Vo-Dinh et al. | 128/665 |
| 5,582,168 A | 12/1996 | Samuels et al. | 128/633 |
| 5,590,660 A | 1/1997 | MacAulay | 128/664 |
| 5,624,847 A | 4/1997 | Lakowicz et al. | 436/68 |
| 5,628,310 A * | 5/1997 | Rao et al. | 600/317 |
| 5,647,368 A | 7/1997 | Zeng et al. | 128/665 |
| 5,692,504 A * | 12/1997 | Essenpreis et al. | 600/316 |
| 5,699,798 A * | 12/1997 | Hochman et al. | 600/420 |
| 5,736,410 A | 4/1998 | Zarling et al. | |
| 5,759,767 A | 6/1998 | Lakowicz et al. | 435/4 |
| 5,792,049 A | 8/1998 | Eppstein et al. | 600/306 |
| 5,818,583 A | 10/1998 | Sevick-Muraca et al. | 600/476 |
| 5,832,931 A * | 11/1998 | Wachter et al. | 128/898 |
| 5,860,421 A | 1/1999 | Eppstein et al. | 128/660.06 |
| 5,865,754 A * | 2/1999 | Sevick-Muraca et al. | 600/476 |
| 5,891,656 A * | 4/1999 | Zarling et al. | 435/7.92 |
| 5,917,190 A | 6/1999 | Yodh et al. | 250/458.1 |
| 5,919,140 A * | 7/1999 | Perelman et al. | 600/476 |
| 5,928,627 A * | 7/1999 | Kiefer et al. | 424/9.6 |
| 5,949,077 A | 9/1999 | Alfano et al. | 250/459.1 |
| 6,070,583 A * | 6/2000 | Perelman et al. | 600/476 |
| 6,216,540 B1 * | 4/2001 | Nelson et al. | 73/633 |
| 6,271,522 B1 | 8/2001 | Lindermeir et al. | 250/341.1 |
| 6,304,771 B1 * | 10/2001 | Yodh et al. | 600/476 |
| 6,321,111 B1 * | 11/2001 | Perelman et al. | 600/477 |
| 6,480,276 B1 | 11/2002 | Jiang | 356/336 |
| 6,671,540 B1 * | 12/2003 | Hochman | 600/431 |
| 7,054,002 B1 * | 5/2006 | Sevick-Muraca et al. | 356/317 |
| 2003/0117622 A1 | 6/2003 | Sevick-Muraca et al. | |
| 2005/0073681 A1 | 4/2005 | Sevick-Muraca et al. | |

FOREIGN PATENT DOCUMENTS

| | | |
|---|---|---|
| GB | 2311366 A | 3/1996 |
| JP | 2-268256 | 1/1990 |
| JP | H07-507472 | 8/1995 |
| WO | WO 95/12132 | 5/1995 |
| WO | WO 97/08538 | 3/1997 |
| WO | WO 99/49312 | 3/1999 |
| WO | WO 00/22414 | 10/1999 |
| WO | WO 02/41760 A2 | 5/2000 |
| WO | WO 01/22063 A1 | 9/2000 |

OTHER PUBLICATIONS

Richard Haskel et al., "Boundary conditions for the diffusion equation in radiative transfer", J. Opt. Soc. Am., A. vol. 11, No. 10. Oct. 1994, pp. 2727-2741.

R. L. Sheridan et al., "Burn depth estimation by use of indocyanine green fluorescence: Initial human trial", Journal of Burn Care & Rehabilitation, vol. 16 No. 4, pp. 1-5.

M. A. O'Leary et al., "Fluorescence lifetime imaging in turbid media", Optics Letters, vol. 21 No. 2, Jan. 1996, pp. 158-160.

Huabei Jiang et al., "Optics image reconstruction using frequency-domain data; simulations and experiments", J. Opt. Soc. Am., vol. 13, No. 2, Feb. 1996, pp. 253-266.

Alwin Dienle et al., "Spatially resolved absolute diffuse refletance measurements for noninvasive determination of the optical scattering and absorption coefficients of biological tissue", Applied Optics, vol. 35, No. 13, May 1996, pp. 2304-2314.

X. D. Li et al., "Fluorescent diffuse photon density waves in homogenous and heterogeneous turbid media; analytic solutions and applications", Applied Optics, vol. 35, No. 19, Jul. 1996, pp. 3746-3758.

Michael Patterson et al., "Applications of time-resolved light scattering measurements to photodynamic therapy dosimetry", Applied Optics 1203-1208.

Michael Patterson et al., "Diffusion equation representation of photon migration in tissue".

Eva Sevick-Muraca et al., "Origin of phosphorescence signals reemitted from tissues", Optics Letters, vol. 19, No. 23, Dec. 1994, pp. 1928-1930.

Christina Hutchinson et al., "Fluorescence lifetime-based sensing in tissues: a computational study", Biophysical Journal, vol. 68, Apr. 1995 pp. 1574-1584.

B. W. Pogue et al., "Initial Assessment of a simple system for frequency domain diffuse optical tomography", Phys. Med. Biol. 40, (1995) 1709-1729.

Stefan Anderson-Engels et al., "Laser induced fluorescence in malignant and normal tissue of rats injected with benzoporphyrin derivative", Photochemistry and Photobiology, vol. 57, No. 6, pp. 978-983, 1993.

Jun Wun et al., "Three-dimensional imaging of objects embedded in turbid media with fluorescence and raman spectroscopy", Applied Optics, vol. 34, No. 18, Jun. 1995 pp. 3425-3430.

Scott R. Fulton, et al., "Time-resolved laser-induced fluorescence spectroscopy for enhanced demarcation of human atherosclerotic plaques", Journal of Photochemistry and Photobiology, (1990) pp. 363-369.

Seth Fraden et al., "Multiple light scattering from concentrated, interacting suspensions", Physical Review letters, vol. 65, No. 4, pp. 512-515.

K. M. Yoo et al., "Imaging objects hidden in scattering media using a fluorescence-absorption technique", Optics Letters, vol. 16, No. 16, 1991, pp. 1252-1254.

R. C. Straight et al., "Application of Charge-coupled device technology for measurement of laser light and fluorescence distribution in tumors for photodynamic therapy", Photochemistry and Photobiology, vol. 53, No. 6, pp. 787-796.

E. M. Sevick et al., "Frequency domain imaging absorbers obscured by scattering", J. Photochem, Photobiol. B:Biol, 16 (1992) pp. 169-185.

Wai S. Poon et al., "Laser-induced Fluorescence Experimental intraoperative delineation of tumor resection margins", J. Neurosurg, vol. 76, Apr. 1992, pp. 679-686.

Brian C. Wilson et al., "Time-dependent optical spectroscopy and imaging for biomedical applications", Proceedings of the IEEE, vol. 80, No. 6, Jun. 1992 pp. 918-930.

A. Knuittel et al., "Acoust-optic scanning and interfering photon density waves for precise localization of an absorbing (or fluorescence) body in a turbid medium", Rev. Sci. Instrum. vol. 64, No. 3, Mar. 1993, pp. 638-644.

R. Cubeddu et al., "Time-gated Fluorescence imaging for the diagnosis of tumors in a murine model", Photochemistry and Photobiology, vol. 57, No. 3, pp. 480-485.

Randall Barbour et al., "A perturbation approach for optical diffusion tomography using continuous-wave and time-resolved data", Medical Optical Tomography, pp. 87-121.

M. A. O'Leary et al., "Reradiation and imaging of diffuse photon density waves using fluorescent inhomogeneities", Journal of Luminescence, (1994) pp. 281-286.

Michael S. Patterson et al., "Mathematical model for time-resolved and frequency-domain fluorescence spectroscopy in biologocal tissues", Applied Optics, vol. 33, No. 10, Apr. 1994, pp. 1963-1974.

David A. Russel et al., "*Continuous noninvasive measurement of InVivo pH in conscious mice*", Photochemistry and Photobiology, vol. 59, No. 3 (1994) pp. 309-313.

Serge Mordon et al., "*In Vivo pH measurement and imaging of tumor tissue using a pH-sensitive fluorescent probe (5,6-carboxyfluorescein): Instrumental and Experimental studies*", Photochemistry and Photobiology, vol. 60, No. 3, pp. 274-279.

Jun Wu et al., "*Time-resolved multichannel imaging of fluorescent objects embedded in turbid media*", Optic Letters, vol. 20, No. 5, Mar. 1995 pp. 489-491.

Sevick-Muraca, et al.; "*Method and System for Detecting Sentinel Lymph Nodes;*" U.S. Appl. 10/618,194; 28 pgs, Jul. 11, 2003.

Stevick-Muraca, et al.; "*Method for Characterizing Particles in Suspension from Frequency Domain Photon Migration Measurements*" U.S. Appl. No. 10/115,271, 59 pgs, Apr. 3, 2002.

Sevick-Muraca, et al.; *Method for Characterizing Particles in Suspension from Frequency Domain Photon Migration Measurements*; U.S. Appl. 11/204,844; 59 pgs, Aug. 16, 2005.

Reynolds, et al., "*Imaging of Spontaneous Canine Mammary Tumors Using Fluorescent Contrast Agents*", Photochemistry and Photobiology, 1999: 79(1): 87-94 (XP-001063376), Apr. 14, 1999.

Gurfinkel, et al., "*Pharmacokinetcs of ICG and HPPH-car for the Detection of Normal and Tumor Tissue Using Fluorescence, Near-Infrared Reflectance Imaging: A Case Study*", Photochemistry and Photobiology, 2000: 72(1): 94-102 (XP-001030699), Apr. 28, 2000.

Thompson, et al., "*Near-infrared fluorescence contrast-enhanced imaging with intensified charge-coupled device homodyne detection: measurement precision and accuracy*", Journal of Biomedical Optics, 2003: 8(1): 111-120 (XP-002301882)klj, Jan. 2003.

Gratton, et al., *A Continuously Variable Frequency Cross-Correlation Phase Fluorometer with Picosecond Resolution*, © Biophysical Society, Biophysical Journal, vol. 44, pp. 315-324, Dec. 1983.

Gratton, et al., *The possibility of a near-infrared optical imaging system using frequency domain method*, Mind Brain Imaging Program, Hamamatsu, Japan, pp. 183-189, Aug. 5-Oct. 1990.

Sevick, et al., *Quantitation of Time-and Frequency-Resolved Optical Spectra for the Determination of Tissue Oxygenation*, Analytical Biochemistry 195, © 1991 Academic Press Inc., pp. 330-351, 1991.

Fishkin, et al., *Propagation of photon-density waves in strongly scattering media containing an absorbing semi-infinite plane bounded by a straight edge*, vol. 10, No. 1, © 1993 Optical Society of America, pp. 127-140, Jan. 1993.

Tromberg, et al., *Properties of photon density waves in multiple-scattering media*, vol. 32, No. 4, Applied Optics, pp. 607-616, Feb. 1, 1993.

Madsen, et al., *Determination of the optical properties of the human uterus using frequency-domain photon migration and steady-state techniques*, Phys. Med. Biol. 39, © 1994 IOP Publishing Ltd., pp. 1191-1202, 1994.

Fantini, et al., *Quantitative determination of the absorption spectra of chromophores in strongly scattering media: a light-emitting-diode based technique*, Applied Optics, vol. 33, No. 22, pp. 5204-5213, Aug. 1, 1994.

Fishkin, et al., *Frequency-domain method for measuring spectral properties in multiple-scattering media: methemoglobin absorption spectrum in a tissuelike phantom*, Applied Optics, vol. 34, No. 7, pp. 1143-1155, Mar. 1, 1995.

Pham, et al., *Broad bandwidth frequency domain instrument for quantitative tissue optical spectroscopy*, Review of Scientific Instruments, vol. 71, No. 6, © 2000 American Institute of Physics, pp. 2500-2513, Jun. 2000.

Hawrysz, et al., *Developments Toward Diagnostic Breast Cancer Imaging Using Near-Infrared Optical Measurements and Fluorescent Contrast Agents*[1], Review Article, Neoplasia, vol. 2, No. 5, © 2000 Nature America, Inc., pp. 388-417, Sep.-Oct. 2000.

Tromberg, et al., *Non-invasive measurements of breast tissue optical properties using frequency-domain photon migration*, Phil. Trans. R. Soc. Lond. B, © 1997 The Royal Society, pp. 661-668.

Muzzio, et al., *Sampling practices in powder blending*, Research papers, International Journal of Pharmaceutics 155, © 1997 Elsevier Science B.V., pp. 153-178.

Fishkin, et al., *Frequency-domain photon migration measurements of normal and malignant tissue optical properties in a human subject*, Applied Optics, vol. 36, No. 1, pp. 10-20, Jan. 1, 1997.

Sevick-Muraca, et al., *Photon-Migration Measurement of Latex Size Distribution in Concentrated Suspensions*, Particle Technology and Fluidization, AIChE Journal, vol. 43, No. 3, pp. 655-664, Mar. 1997.

Richter, et al., *Particle Sizing Using Frequency Domain Photon Migration*, Part. Part. Syst. Charact. 15, © Wiley-VCH Verlag GmbH, D-69469 Weinheim, pp. 9-15, 1998.

Ramanujam, et al., *Sources of phase noise in homodyne and heterodyne phase modulation devices used for tissue oximetry studies*, Review of Scientific Instruments, vol. 69, No. 8, © 1998 American Institute of Physics, pp. 3042-3054, Aug. 1998.

Chance, et al., Review Article, *Phase measurement of light absorption and scatter in human tissue*, Review of Scientific Instruments, vol. 69, No. 10, © 1998 American Institute of Physics, pp. 3457-3481, Oct. 1998.

Banerjee, et al.; *Probing Static Structure of Colloid-Polymer Suspensions with Multiply Scattered Light*, Journal of Colloid and Interface Science 209, © 1999 by Academic Press, pp. 142-153, 1999.

Shinde, et al., *Investigation of static structure factor in dense suspensions by use of multiply scattered light*, Applied Optics, vol. 38, No. 1, © 1999 Optical Society of America, pp. 197-204, Jan. 1, 1999.

Gerken, et al., *High-precision frequency-domain measurements of the optical properties of turbid media*, Optics Letters, vol. 24, No. 14, © 1999 Optical Society of America, pp. 930-932, Jul. 15, 1999.

Shinde, et al., *Frequency-Domain Photon Migration Measurements for Quantitative Assessment of Powder Absorbance: A Novel Sensor of Blend Homogeneity*, Research Articles, © 1999 American Chemical Society and American Pharmaceutical Association, Journal of Pharmaceutical Sciences, vol. 88, No. 10, pp. 959-966, Oct. 1999.

Banerjee, et al., *Assessment, of $S(0,\emptyset)$ from multiply scattered light*, Journal of Chemical Physics, vol. 111, No. 20, © 1999 American Institute of Physics, pp. 9133-9136, Nov. 22, 1999.

Sun, et al., "*Particle Characterization of Colloidal Suspension at High Volume Fractions Using Frequency Domain Photon Migration,*" 6th World Congress of Chemical Engineering, Melbourne 2001, pp. 4/15-12/15, 2001.

Sun, et al., "*Inversion Algorithms for Particle Sizing with Photon Migration Measurements,*" Fluid Mechanics and Transport Phenomena, AIChE Journal, vol. 47, No. 7, pp. 1487-1498, Jul. 2001.

Hutchinson, Christina L., et al., "*Fluorescence-Lifetime Determination in Tissues or Other Scattering Media from Measurement of Excitation and Emission Kinetics*", Applied Optics, vol. 35, No. 13, pp. 2325-2332, May 1, 1996.

Sun, et al., "*Approach for Particle Sizing in Dense Polydisperse Colloidal Suspension Using Multiple Scattered Light,*" XP-001126299, Langmuir 2001, 17, 2001 American Chemical Society, pp. 6142-6147, Sep. 8, 2001.

Isayev, K, et al., "*Study of Thermophysical Properties of a Metal-Hydrogen System,*" International Journal of Hydrogen Energy, vol. 21, No. 11-12, Nov. 12, 1996, pp. 1129-1132.

Panda, et al., "*Generalized B-Spline Signal Processing,*" European Journal Devoted to the Methods and Applications of Signal Processing, Elsevier Science Publishers, B.V. Amsterdam, NL, vol. 55, No. 1, Nov. 1, 1996 XP004016005, pp. 1-14.

PCT Invitation to Pay Additional Fees (PCT Article 17(3)(a) and Rule 40.1), Annex to Form PCT/ISA/206 Communication Regarding to the Results of the Partial International Search Authority, regarding PCT/US02/10433, filed Apr. 3, 2002, Applicant's reference 017575.0748, 6 pages, Nov. 29, 2002.

PCT International Search Report in International Application No. 02/10433, dated Jun. 16, 2003, 10 pages.

Thompson, et al., "*Near-infrared fluorescence contrast-enhanced imaging with area illumination and area detection: the forward imaging problem*", Applied Optics, 2003: 42(19): 4125-4136 (XP-002301883), Jul. 1, 2003.

Notification of Transmittal of the International Search Report and the Written Opinion of the International Searching Authority for International Application No. PCT/US2004/019792, filed Jun. 18, 2004 (14 pages), Nov. 8, 2004.

Houston, et al., "Sensitivity and Depth Penetration of Continuous Wave Versus Frequency-domain Photon Migration Near-infrared Fluorescence Contrast-enhanced Imaging," Photochemistry and Photobiology, 2003, vol. 77(4), pp. 420-430.

Ntziachristos, et al. "In Vivo Tomographic Imaging of Near-Infrared Fluorescent Probes," Molecular Imaging, vol. 1(2), pp. 82-88, Apr. 2002.

Pan, et al., *Volume of Pharmaceutical Powders Probed by Frequency-Domain Photon Migration Measurements of Multiply Scattered Light*, Analytical Chemistry 2002, vol. 74, No. 16, © 2002 American Chemical Society, pp. 4228-4234, Aug. 15, 2002.

Richter, et al., *Characterization of concentrated colloidal suspensions using time-dependent photon migration measurements*, Reprinted from Colloids And Surfaces An International Journal, A: Physicochemical and Engineering Aspects, © 2000 Elsevier Science B.V., pp. 163-173, plus cover.

PCT Patent Application No. PCT/US99/23709 filed Oct. 8, 1999, entitled "*Characterization of Luminescence in a Scattering Medium*," currently pending.

Mayer, Ralf H., et al., "Measurement of the Fluorescence Lifetime in Scattering Media by Frequency-Domain Photon Migration", Applied Optics, vol. 38, No. 22, pp. 4930-4938, Aug. 1, 1999.

Cerussi, Albert E., et al., "Experimental Verification of a Theory for the Time-Resolved Fluorescence Spectroscopy of Thick Tissues", Applied Optics, vol. 36, No. 1, pp. 116-124, Jan. 1, 1997.

\* cited by examiner

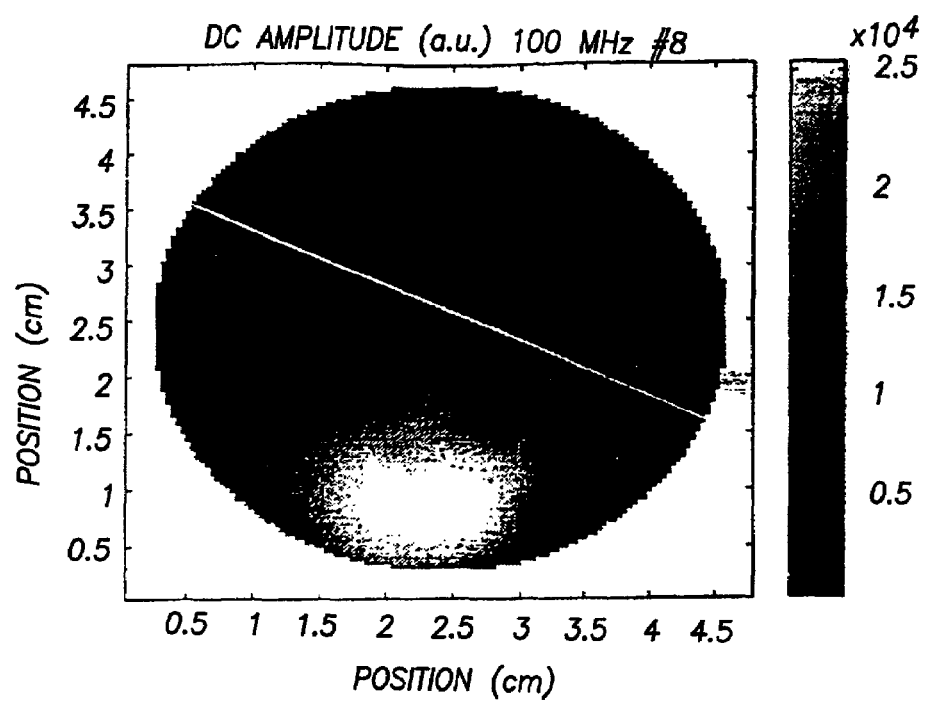
FIG.22C
FIG.22D
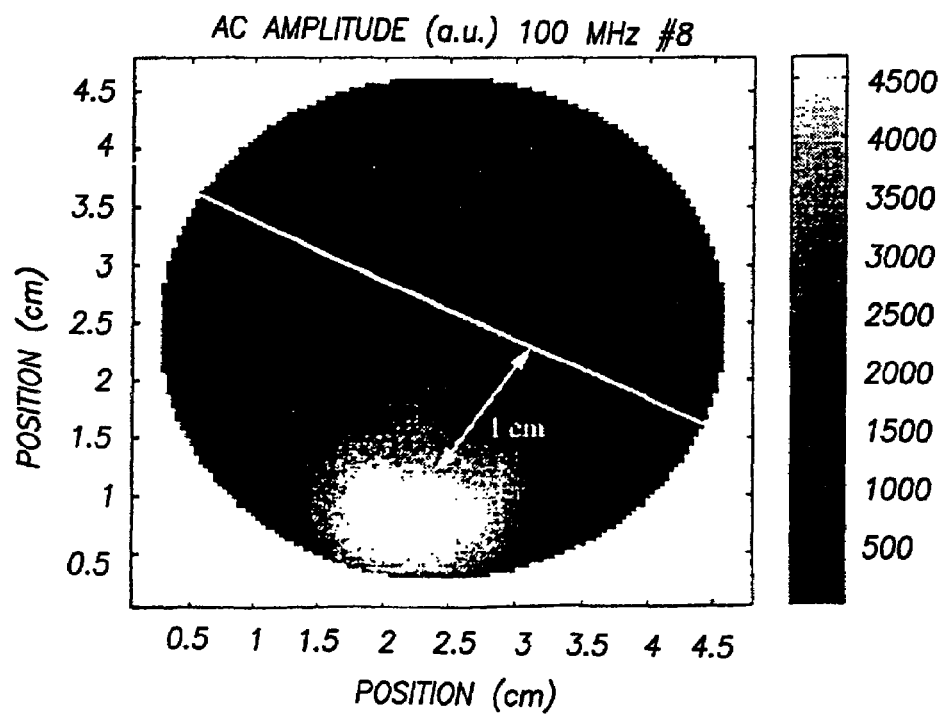

IMAGING OF LIGHT SCATTERING TISSUES WITH FLUORESCENT CONTRAST AGENTS

CROSS-REFERENCE TO RELATED APPLICATION

This application is a continuation of U.S. application Ser. No. 09/367,148, filed Nov. 22, 1999, now abandoned which was the National Stage of International Application No. PCT/US/98/02354, filed Feb. 6, 1998, which claims the benefit of U.S. Provisional Application No. 60/039,318, filed Feb. 7, 1997 and which is a continuation-in-part of Ser. No. 08/702,060, filed Aug. 23, 1996, now U.S. Pat. No. 5,865,754.

BACKGROUND OF THE INVENTION

The present invention relates to spectroscopic imaging of heterogeneous light scattering tissue, and more particularly, but not exclusively, relates to in vivo imaging by mapping a fluorescence characteristic of the tissue.

The early detection of disease promises a greater efficacy for therapeutic intervention. In recent years, noninvasive techniques have been developed which have improved the ability to provide a reliable and early diagnosis of various afflictions by detecting biochemical changes in the tissue of a patient. For example, Magnetic Resonance Imaging (MRI) has successfully monitored the relaxation of spin states of paramagnetic nuclei in order to provide biomedical imaging and biochemical spectroscopy of tissues. Unfortunately, the complexity and expense of MRI diagnostics limit its availability—especially as a means of routine monitoring for disease.

Another powerful analytical technique with an increasing number of applications in the biological sciences is fluorescence spectroscopy. Applications of fluorescence spectroscopy include biomedical diagnostics, genetic sequencing, and flow cytometry. As exemplified by U.S. Pat. Nos. 5,421,337 to Richards-Kortum et al. and U.S. Pat. No. 5,452,723 to Wu et al., several investigators have suggested various procedures to differentiate diseased and normal tissues based on fluorescence emissions through noninvasive external measurements or minimally invasive endoscopic measuring techniques. Unfortunately, these procedures generally fail to provide a viable spatial imaging procedure. One reason imaging based on fluorescence has remained elusive is that meaningful relational measurements of fluorescence characteristics from a random, multiply scattering media, such as tissue, are difficult to obtain. For example, fluorescent intensity, which is a function of the fluorescent compound (or fluorophore) concentration or "uptake" is one possible candidate for imaging; however, when this property is used in an optically dense medium, such as a particulate (cell) suspension, powder, or tissue, the local scattering and absorption properties confound measured fluorescent intensities.

Besides intensity, other properties of selected fluorophores such as fluorescent quantum efficiency and lifetime are also sensitive to the local biochemical environment. As used herein, "fluorescent quantum efficiency" means the fractional number of fluorescent photons emitted for each excitation photon absorbed or the fraction of decay events which result in emission of a fluorescent photon. "Fluorescent lifetime," as used herein, is defined as the mean survival time of the activated fluorophore or the mean time between the absorption of an excitation photon and emission of a fluorescent photon. Like intensity, measurement of these fluorescence characteristics is often limited to well-defined in vitro applications in the research laboratory or in flow cytometry where issues such as scattering, absorption, and changing fluorophore concentrations can be controlled or measured. Moreover, these limitations generally preclude meaningful fluorescence-based imaging of hidden tissue heterogeneities, such as tumors or other diseased tissue regions, which cannot be detected by visual inspection.

With the development of techniques to interrogate tissues using fluorescence in the near-infrared red (NIR) wavelength regime, noninvasive detection of diseased tissues located deep within normal tissues may also be possible since NIR excitation and emission light can travel significant distances to and from the tissue-air interface. U.S. Pat. Nos. 5,213,105 to Gratton et al. and U.S. Pat. No. 5,353,799 to Chance are cited as further background concerning NIR interrogation. As in the case of MRI, x-ray, CT, and ultrasound imaging modalities, there is a potential to enhance NIR fluorescence imaging techniques with contrast agents. Typically, contrast agents for in vivo imaging have depended upon preferential uptake into diseased tissue to provide the desired imaging enhancement by absorbing the interrogating radiation. The light absorbing tissue provides an enhanced spatial variation in measured intensity of the radiation to improve image contrast. In the case of a fluorescent contrast agent, the intensity of fluorescent light emitted in response to the absorption may provide this intensity variation. Generally, the larger the difference in spatial variation, as artificially imposed by a contrast agent, the more improved the reconstructed image of interior tissues. Nonetheless, the effectiveness of exogenous contrast agents depends greatly upon the selectivity of the agent for the tissue region of interest. Unfortunately, targeted and site specific delivery of drugs and contrast agents has historically been a limiting factor in both therapeutics and diagnostic imaging. Consequently, additional mechanisms for inducing contrast that are not dependent solely upon tissue selectively of the agent would be advantageous.

Thus, a need remains for a technique to noninvasively image multiply scattering tissue based on one or more fluorescence characteristics. Preferably, this technique includes the implementation of exogenous contrast agents with image-enhancing properties beyond preferential absorption of the interrogating radiation. The present invention satisfies this need and provides other advantages.

SUMMARY OF THE INVENTION

The present invention relates to spectroscopic imaging of heterogeneous, light scattering materials. Several aspects of the invention are novel, nonobvious, and provide various advantages. While the actual nature of the invention covered herein can only be determined with reference to the claims appended hereto, certain features which are characteristic of the present invention are described briefly as follows.

One feature of the present invention is a technique for imaging a heterogeneous light scattering material. This technique includes exposing the surface of a material to light from a light source and detecting an emission in response. A spatial variation of a fluorescence characteristic of the material is determined as a function of the emission with a processor. The spatial variation may be characterized by a set of values representative of the fluorescence characteristic as a function of position. An image is generated in accordance with the spatial variation that corresponds to the heterogeneous composition of the material. This technique may be applied in vivo to biologic tissue using external or endoscopic instrumentation to detect heterogeneities indicative of disease. The technique may include the introduction of a fluorescent contrast agent into the material. The fluorescence characteristic detected may be fluorescence lifetime, fluorescence quantum efficiency, a fluorophore absorption coefficient, fluorescent yield (a function of fluorescent quantum efficiency and fluorophore absorption), or another fluorescence characteristic known to those skilled in the art.

Another feature includes introducing a fluorescent contrast agent into a biologic tissue. This contrast agent has a predetermined lifetime and the tissue multiply scatters light with a mean time-of-flight between scattering events. The lifetime and the mean time-of-flight are within a factor of about ten of each other. The tissue is exposed to an excitation light with a predetermined time-varying intensity and a light emission is detected from the tissue in response to this exposure. An image of the tissue is generated by mapping spatial variation of a level of a fluorescence characteristic of the tissue from the light emission in accordance with a mathematical relationship modeling multiple light scattering behavior of the tissue.

In a further feature, the agent may be selected in accordance with a predetermined relationship between degree of image contrast and at least one of fluorescence yield or the fluorescence lifetime. Preferably, the lifetime is in a range of about 0.1 to 10 nanoseconds (ns). A more preferred range is 0.5 to 5 ns. A still more preferred range is about 0.2 to 2 ns. A most preferred value for the lifetime is about 1 ns.

An additional feature includes evaluating ability of a number of fluorescent agents to provide image contrast between different tissue types. This evaluation includes determining a relationship between degree of image contrast and at least one of fluorescence lifetime or fluorescence yield of the agent. One of the agents is selected based on the evaluation. The selected agent is provided for introduction into a biologic tissue to enhance imaging performed in accordance with a mathematical expression modeling the behavior of multiply scattered light traveling through the tissue.

In still another feature, a biologic tissue is exposed to a first excitation light and a first emission is detected from the tissue in response to the first excitation light. A fluorescent contrast agent is introduced into the tissue after this detection and the tissue is then exposed to a second excitation light. A second emission is sensed in response to the second excitation light. Data corresponding to the first emission is compared with data corresponding to the second emission to evaluate contrast provided by the agent. Contrast may be determined as a function of at least one of fluorescence lifetime, fluorescence yield, or quantum efficiency. For a frequency domain form of this evaluation, the image contrast may be evaluated in terms of phase contrast or modulation contrast Moreover, the wavelength of the first excitation light may be selected to be generally the same as the wavelength of the fluorescent light emitted by the agent in response to the second excitation light.

Accordingly, it is one object of the present invention to map a fluorescent property of a light scattering material that varies with the heterogeneous composition of the material to generate a corresponding image.

It is another object of the present invention to provide a spectroscopic technique for noninvasively monitoring fluorescent properties of hidden tissue volumes in a living organism and to monitor selected metabolites of an organism in vivo.

Yet another object is to provide a technique to select and design fluorescent contrast agents who improve contrast for photon migration based imaging. This technique may include the selection of contrast enhancing properties that are not solely dependent upon uptake.

Further objects, features, aspects, benefits, and advantages of the present invention will become apparent from the drawings and description contained herein.

BRIEF DESCRIPTION OF THE DRAWINGS

FIGS. 22A-22D are computer-generated gray scale images depicting spatial variation for in vivo tissue imaging of a dog treated with an ICG contrast agent in terms of modulation phase-shift, modulation ratio (AC/DC), average DC intensity, and AC modulation amplitude, respectively.

DESCRIPTION OF PREFERRED EMBODIMENTS

Figure 1:
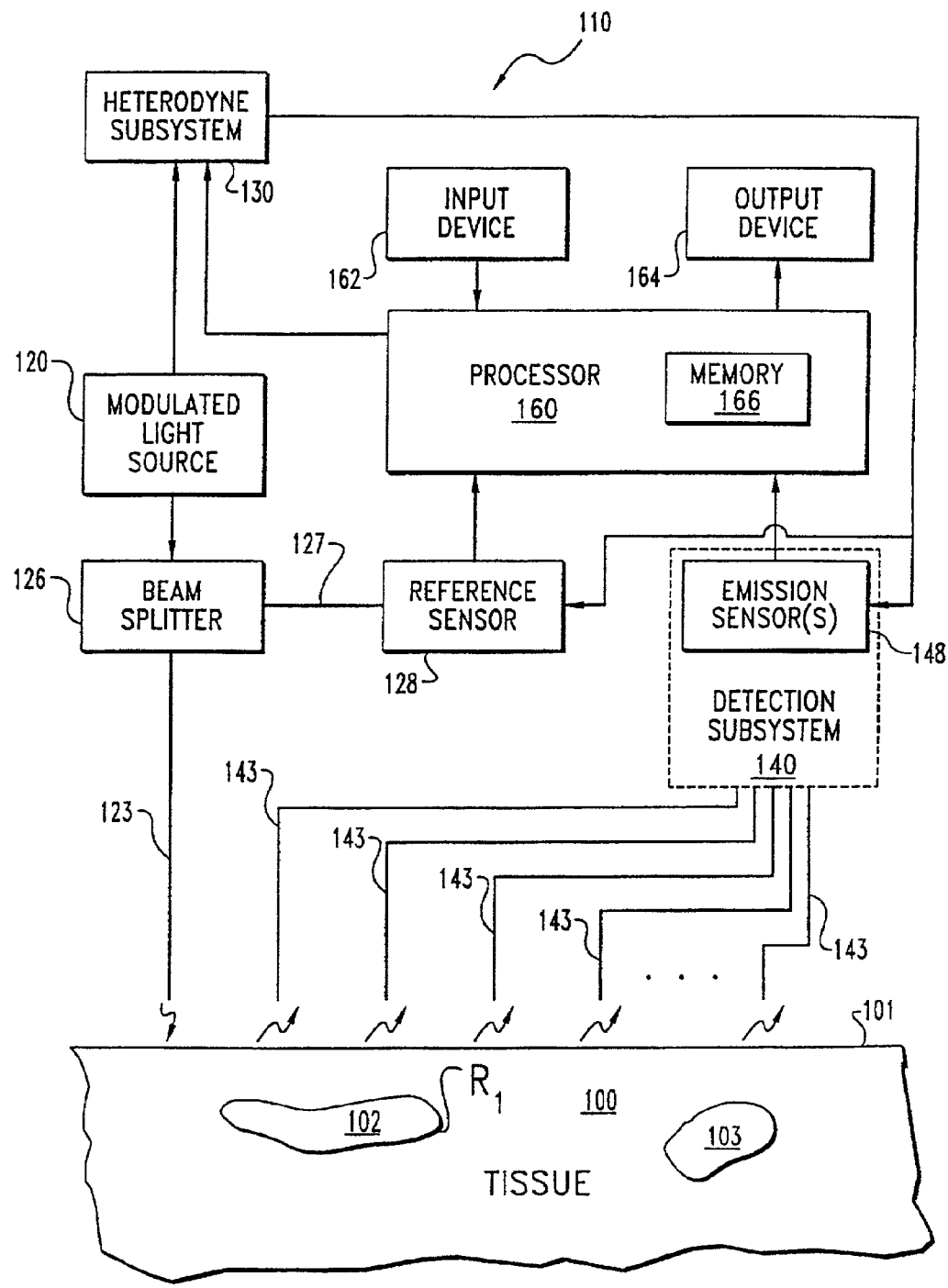
FIG. 1 is a schematic illustration of a system of one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described techniques, methods, systems, and devices, and any further applications of the principles of the invention as described herein are contemplated as would normally occur to one skilled in the art to which the invention relates.

FIG. 1 depicts system 110 of the present invention for fluorescent imaging of tissue 100. Tissue 100 has surface 101 and a heterogeneous composition as represented by regions 102, 103 underlying surface 101. Heterogeneities 102, 103 are generally not detectable by visual inspection of surface 101.

System 110 includes modulated light source 120 to supply an intensity-modulated excitation light of predetermined frequency and wavelength to tissue 100 via optic fiber 123. Preferably, source 120 is a laser diode of conventional design with a modulated output in the 1-500 MHz frequency range and a monochromatic output in the 100 to 1000 nanometer (nm) wavelength range. The specific wavelength is selected to excite a designated fluorophore in tissue 100. Beam splitter 126 may be employed to direct a small portion of the excitation signal to reference sensor 128 for processing purposes.

System 110 also includes detection subsystem 140 which has optic fibers 143 to detect photons emitted from tissue 100 from a number of corresponding detection sites. Subsystem 140 includes one or more emission sensors 148. Detection subsystem 140 also includes an interference filter to obtain a selected emission wavelength corresponding to emission of a designated fluorophore in tissue 100. In one embodiment, subsystem 140 includes a single sensor 148 and the signals from fibers 143 are multiplexed. Preferably, sensors 128, 148 are Photo-multiplier Tubes (PMTs) or photodiode detectors but other sensor varieties, such as image intensifiers and charge-coupled devices, are also contemplated.

Sensors 128, 148 and source 120 are operatively coupled to heterodyne subsystem 130. Subsystem 130 is configured to obtain information about the phase, AC, and DC intensity of light detected with sensor 128 relative to light detected with the sensor 148 using conventional heterodyning techniques. In one embodiment, heterodyne subsystem 130 includes a signal synthesizer phase-locked to the repetition rate of a laser used for source 120. For this embodiment, subsystem 130 includes an amplifier to gain modulate sensors 128, 148 at a harmonic of a laser repetition rate (when a pulsed laser is used) or at the modulation frequency (when a modulated laser diode is used) plus an offset to provide the desired heterodyning. In one variation of this embodiment, an 80 MHz pulsed laser repetition rate is divided down to 10 MHz and input to the synthesizer, and a heterodyning offset of 100 kHz is input to the amplifiers for sensors 128, 148.

Sensors 128, 148 are operatively coupled to processor 160. Processor 160 includes input/control device 162, output device 164, and memory 166. Processor 160 may be an electronic circuit comprised of one or more components. Similarly, processor 160 may be comprised of digital circuitry, analog circuitry, or both. Also, processor 160 may be programmable, an integrated state machine, or a hybrid combination thereof. Preferably, input device 162 is a keyboard or input control of a conventional variety, and output device 166 is a Cathode Ray Tube (CRT) based video display, printer, or other image display system known to those skilled in the art. Memory 166 is preferably of the electronic (e.g. solid state), magnetic, or optical variety of the type readily available for use with electronic controllers or processors. Furthermore, Memory 166 may include an optical disk memory (CD), electromagnetic hard or floppy disk media, or a combination of these.

Figure 2:
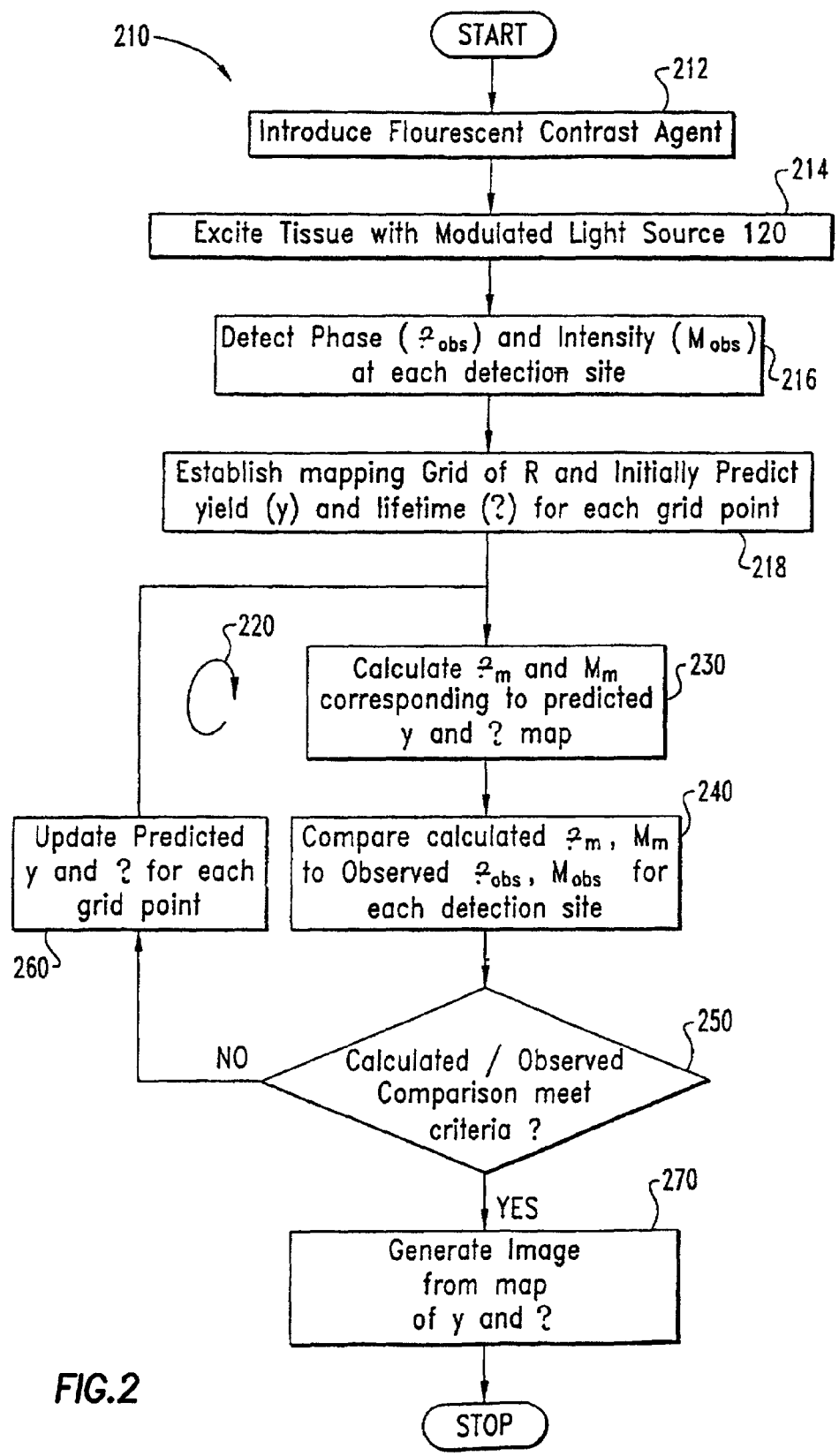
FIG. 2 is a flow chart of a process utilizing the system of FIG. 1.

FIG. 2 depicts one mode of operation of system 110 as process 210. Process 210 includes mapping the spatial variation of fluorescence yield and lifetime with processor 160 and generating an image signal in accordance with the map. Output device 164 is configured to display an image in response to the image signal. Process 210 begins by introducing a fluorescent contrast agent into tissue 100 in stage 212. This agent provides a source of fluorescent emission for detection by subsystem 240. The configuration of the modulated light source 120, heterodyne subsystem 130, and detection subsystem 140 is designed to accommodate the excitation and emission properties of the selected fluorescent agent. In other embodiments, endogenous fluorophores may be alternatively or additionally employed and system 110 adjusted accordingly.

In stage 214, light source 120 configured according to the selected fluorophore excites tissue 100. In stage 216, the phase, $\theta_{obs}$, and log of AC intensity, $M_{obs}$, of the emission at each detection site "i" relative to the excitation light from source 120 are determined at the heterodyne (or offset) frequency. For "Di" number of detection sites, the detected or observed phase and AC intensity are indexed by "i" using the following notation: $(\theta_{obs})_i$ and $(M_{obs})_i$, respectively. Processor 160 stores the relative phase and AC intensity information in memory 166.

In stage 218, a two dimensional grid is established for an area of tissue 100 selected for imaging, and a matrix of grid points is established and indexed by "j". A uniform seed value for the fluorescent yield, $y_j = (\eta\mu_{a_{x \to m}})_j$, and the fluorescent lifetime, $(\tau)_j$, at each grid point j is assigned. These values are an initial homogeneous guess of the yield and lifetime values, which are modified in later stages. The term "$\eta$" is the quantum efficiency of the fluorophore which varies with the environment of the surrounding of the fluorophore. The term "$\mu_{a_{x \to m}}$" is the absorption coefficient for the fluorophore and is the product of the extinction coefficient of the fluorophore based on the natural log and the concentration of the fluorophore. As a result, the yield, $y = \eta\mu_{a_{x \to m}}$, is influenced by the surrounding metabolism and the uptake of the fluorophore. The uptake of certain known fluorophores vary with the type and condition of host tissue, providing another fluorescence characteristic useful to detect disease. The contrast provided by these properties is largely independent of fluorophore concentration. The initial estimate of fluorescent yield and lifetime are stored in memory 166 by processor 160 for later use.

After establishing this initial estimate of the fluorescence characteristics of yield, $\eta\mu_{a_{x \to m}}$, and lifetime, $\tau$, processing loop 220 is entered in stage 230. Preferably, the stages of processing loop 220 are executed by processor 160 via preprogrammed software, dedicated hardware, or a combination of both as appropriate. To aid in understanding various mathematical aspects of process 210 and loop 220, the following table of selected variables is listed:

| | |
|---|---|
| c | velocity of light in a vacuum; |
| D(r) | optical diffusion coefficient; |
| Di | number of detection sites; |
| f | modulation frequency; |
| I | identity matrix; |
| i | detection site index; |
| J | Jacobian matrix relating the sensitivity at each grid point, j, to the response at each detection site; |
| j | grid point index; |
| $J_{j,i}$ | individual elements of the Jacobian matrix J; |
| k | source index; |
| M | log of AC intensity of modulated fluorescent light position; |
| m | index to multiple modulation frequencies; |
| n | average index of refraction; |
| r | position (in two or three dimensions); |
| Sk | number of modulated light sources; |
| S(r, ω) | source term, for the modulated light at position r and frequency ω; |
| Greek | |
| $\chi^2$ | merit function representing the least squares error; |
| $\phi_x(r, \omega)$ | complex number representing photon flux in the Frequency domain at position r and frequency ω; |
| η | quantum efficiency of fluorescent probe or dye; |
| $\mu_a$ | average absorption coefficient; |
| $\mu_{a_m}$ | absorption coefficient of the fluorescence light by both the nonfluorescing chromophores and fluorophore: |
| $\mu_{a_x}$ | absorption coefficient of the excitation light by both the nonfluorescing chromophores and fluorophore; |
| $\mu_{a_{x \to c}}$ | adsorption coefficient due to nonfluorescing chromophores; |
| $\mu_{a_{x \to m}}$ | adsorption coefficient of excitation light by fluorophores; |
| $\mu'_s$ | effective scattering coefficient; |
| θ | phase-shift of one modulated light wave to another; |
| τ | lifetime of activated probe or dye at location r; |
| ω | angular modulation frequency, given by 2πf; |
| Subscripts | |
| obs | observed or experimental data; |
| x | excitation light; and |
| m | fluorescence or emission light. |

In stage 230, phase and relative AC intensity at each detection site "i" is calculated as a function of the initial estimates of yield and lifetime for each grid point j. The calculated phase and intensity are represented at each detection site i as $(\theta_m)_i$ and $(M_m)_i$, respectively. The values for $(\theta_m)_i$ and $(M_m)_i$ are determined using the diffusion equation approximation of the radiative transport equation. The diffusion equation approximation describes the spatial and temporal transport of light in tissues or multiply scattering media. A coupled frequency domain diffusion equation can be used to predict the excitation and emission fluence rates, $\Phi_x(r, \omega)$ and $\Phi_m(r, \omega)$, respectively, at any location r within the selected grid of tissue 100 via equations (1) and (2):

$$\nabla \cdot [D_x(r)\nabla\Phi_x(r,\omega)] - [\mu_{a_x}(r) + i\omega/c_n]\Phi_x(r,\omega) + S_x(r,\omega) = 0 \quad (1)$$

$$\nabla \cdot [D_m(r)\nabla\Phi_m(r,\omega)] - [\mu_{a_m}(r) + i\omega/c_n]\Phi_m(r,\omega) + S_m(r,\omega) = 0 \quad (2)$$

The source term for the excitation light $S_x(r,\omega)$ is due to the sinusoidally modulated light at an angular frequency ω=2πf where f is typically in the MHz frequency range. The first term in both of the diffusion equations (1) and (2) represents the diffusive or "random-walk" transport of multiply scattered light where $D_{x,m}$ is the optical diffusion coefficient of equation (3) as follows:

$$D_{x,m} = [3(\mu_{a_{x,m}} + \mu'_{s_{x,m}})]^{-1} \quad (3)$$

and $\mu_a$ and $\mu'_s$ are the absorption and isotropic scattering coefficients, respectively, for tissue 100, the medium of interest. Multiple scattering of light occurs when $\mu'_s >> \mu_a$; where $\mu_a$ indicates the ability to absorb light and $\mu'_s$ indicates the ability to scatter light for a given material at a given wavelength. As used herein, "multiply scattered light" refers to light that travels at least five (5) times the mean isotropic scattering length, defined as $1/\mu'_s$.

Because these optical properties are dependent on the wavelength of light, the coefficients generally differ for the excitation light from source 120 (subscript x) and fluorescent emission detected with subsystem 140 (subscript m). The total absorption coefficient at the excitation wavelength, $\mu_{a_x}$, is due to contributions from nonfluorescing chromophores as well as from fluorophores responsive to the excitation wavelength. The total absorption coefficient is given by the sum of absorption coefficients due to nonfluorescing chromophores, $\mu_{a_{x \to c}}$, and fluorophores $\mu_{a_{x \to m}}$. Generally it may be assumed that the absorption experienced at the fluorescent wavelength is due primarily to nonfluorescing chromophores. The velocity of light in tissue is $c_n=c/n$ where n is the average index of refraction. The source term for the fluorescent emission is dependent on the excitation light fluence, $\Phi_x(r, \omega)$ and is given by equation (4) as follows:

$$S_m(r,\omega)=\eta\mu_{a_{x\to m}}(r)\Phi_x(r,\omega)[(1-i\omega\tau(r))/(1+\omega^2\tau(r)^2)] \qquad (4)$$

This term arises from the Fourier transform of the fluorescence decay term in the time domain following an incident pulse of excitation light where: $\tau$ is the fluorophore lifetime, $\eta$ is the quantum efficiency, and the absorption coefficient, $\mu_{a_{x \to m}}$, is the product of the extinction coefficient based on natural log and the concentration of the fluorophore in the ground state. As previously indicated, the combined product, $\eta\mu_{a_{x \to m}}$, is termed the fluorescent yield, y, and is proportional to the generated fluorescence fluence. Substitution of equation (4) into equation (2) facilitates determination of $\Phi_m$ for each grid point "j." The solution of the diffusion equations (1) and (2) for the two-dimensional area defined by the grid points "j" may be readily extended to three dimensions to estimate spatial variation of one or more fluorescence characteristics in a selected volume with "r" corresponding to position in three dimensions.

Both diffusion equations (1) and (2) are linear complex elliptic equations that can be solved as boundary value problems for the complex quantities $\Phi_x(r, \omega)$ and $\Phi_m(r, \omega)$. This solution employs the method of finite differences to create corresponding finite difference equations. These difference equations are utilized to obtain an approximate solution at each grid point, j. This method of solution is described in other contexts in Fulton et al., *Multigrid Method for Elliptic Problems, A Review*, 114 American Meteorological Society pp. 943-59 (May 1986); and B. W. Pogue et al., *Initial Assessment of a Simple System for Frequency Domain Diffuse Optical Tomography*, 40 Physics in Medicine and Biology pp. 1709-1729 (1995). One preferred method of performing this solution is with the MUD-PACK routines described in Adams, J. C., *MUDPACK: Multigrid Portable Fortran Software for the Efficient Solution of Linear Elliptic Partial Differential Equations*, 34 App. Math Comp. p. 133 (1989). For the solution of the diffusion equations, it is assumed that $\Phi_{m,x}(r,\omega)=0$ on the surface 101 of tissue 100 which is known as the zero fluence boundary condition. It should be recognized that other boundary conditions may be selected and the method of solution varied accordingly.

The diffusion equations (1) and (2) may be solved for a complex number for $\Phi_m$ at each grid point, j. The detected signal at the surface is proportional to the normal component of the gradient of the photon fluence. To approximate the signal at detector site "i" located on surface 101 of tissue 100, the $\Phi_m$ value at an internal grid point closest to the site is selected which follows from the relationship that the normal component of the photon fluence gradient is proportional to $\Phi_m$ just inside surface 101. The calculated phase-lag, $\theta_m$, and the log of AC intensity, $M_m$, at the detection sites "Di" are calculated from the imaginary and real parts of the complex $\Phi_m$ value with respect to the phase and the AC intensity of source 120.

Figure 3:
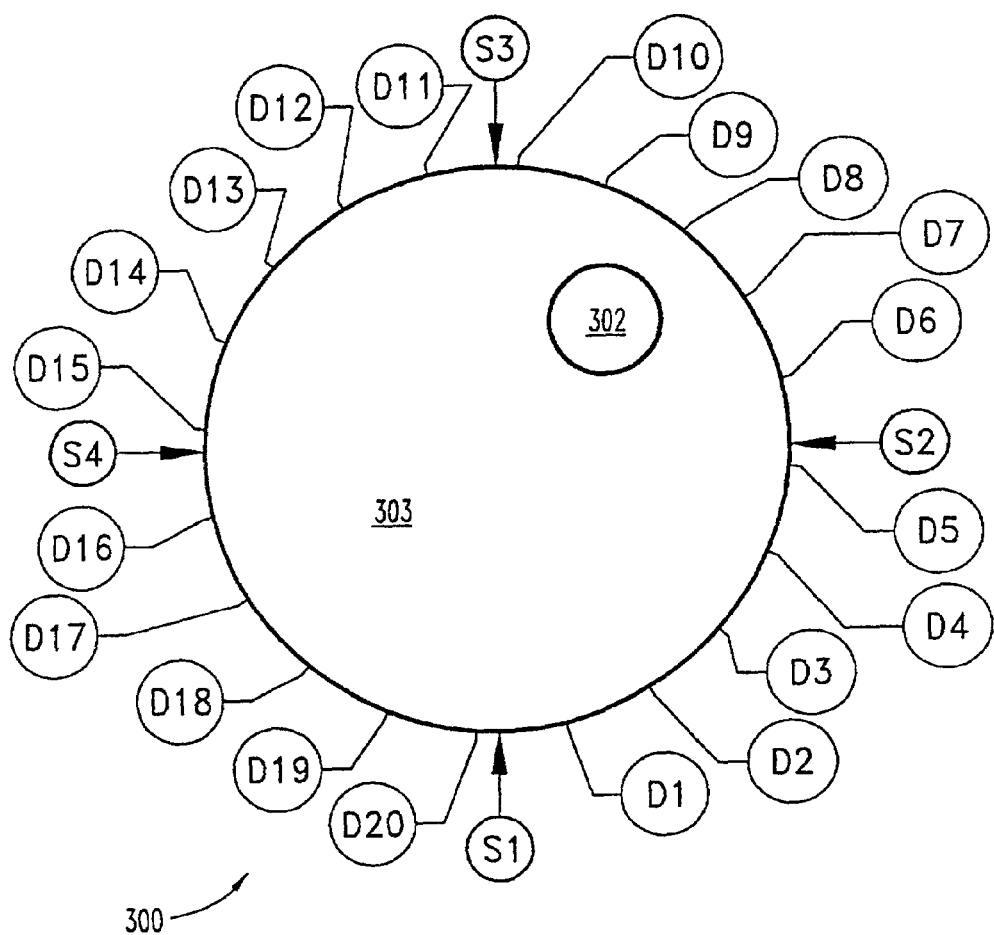
FIG. 3 is a schematic representation of a tissue phantom arrangement used to demonstrate various aspects of the present invention.

The diffusion equations (1) and (2) provide insight into the sensitivity of changing the fluorescent optical properties of tissue 100 on $\theta_m$ and $M_m$ measured at the detector sites i. This insight results from a series of calculations while fixing various parameters of the diffusion equations (1) and (2). These calculations assume circular tissue phantom 300 with an embedded, heterogeneity 302 hidden in phantom background 303 as illustrated in FIG. 3. A two-dimensional grid is established for phantom 300 and may easily be expanded to three dimensions. Under these simulated conditions, a large value is assigned to absorption coefficients for both excitation and fluorescent light at all grid points outside the simulated tissue phantom. The four sources S1-S4 of FIG. 3 (Sk=4) are simulated by assigning an arbitrary complex number at a grid point near the surface closest to each source. The twenty detection sites D1-D20 of FIG. 3 (Di=20) are simulated by using the calculated values determined from $\Phi_m$ at the grid point "j" closest to the detection site. The simulated solutions to diffusion equations (1) and (2) were obtained in two dimensions for a 65×65 grid covering a 100 mm diameter circular tissue phantom 300 with a circular, embedded heterogeneity having a 30 mm diameter and located at the center of the tissue phantom 300 (this location differs slightly from the configuration of heterogeneity 302 of FIG. 3). The simulated measurements of fluorescent phase-shift and AC intensity are reported for 20, equally spaced, circumferentially located detection sites D1-D20. The modulation frequency, f, was set equal to 150 MHz. The optical properties of the heterogeneity and the background are shown in Table 1 as follows:

TABLE 1

| $\mu_{a_x \to 1}$ (mm$^{-1}$) | $\mu_{a_m}$ (mm$^{-1}$) | $\mu_{s_x}$ or $\mu_{s_m}$ (mm$^{-1}$) | $\mu_{a_{x \to q}}$ (mm$^{-1}$) | $\eta\mu_{a_{x \to m}}$ back-ground (mm$^{-1}$) | $\tau$ back-ground (ns) | frequency (MHz) |
|---|---|---|---|---|---|---|
| $\mu_{a_{x \to c}} + \mu_{a_{x \to m}}$ | 0.0 | 1.0 | 0.0 | $1.0 \times 10^{-5}$ | 1.0 | 150.0 |

Figure 4:
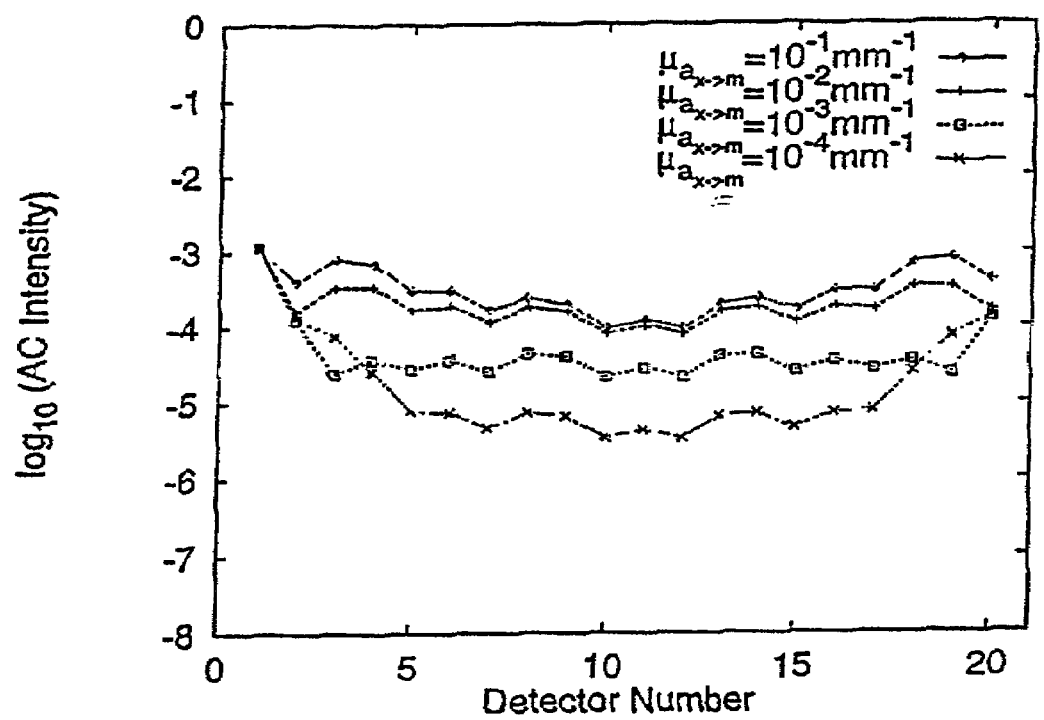
FIGS. 4-7 graphically depict selected properties of equations used in the present invention.
Figure 5:
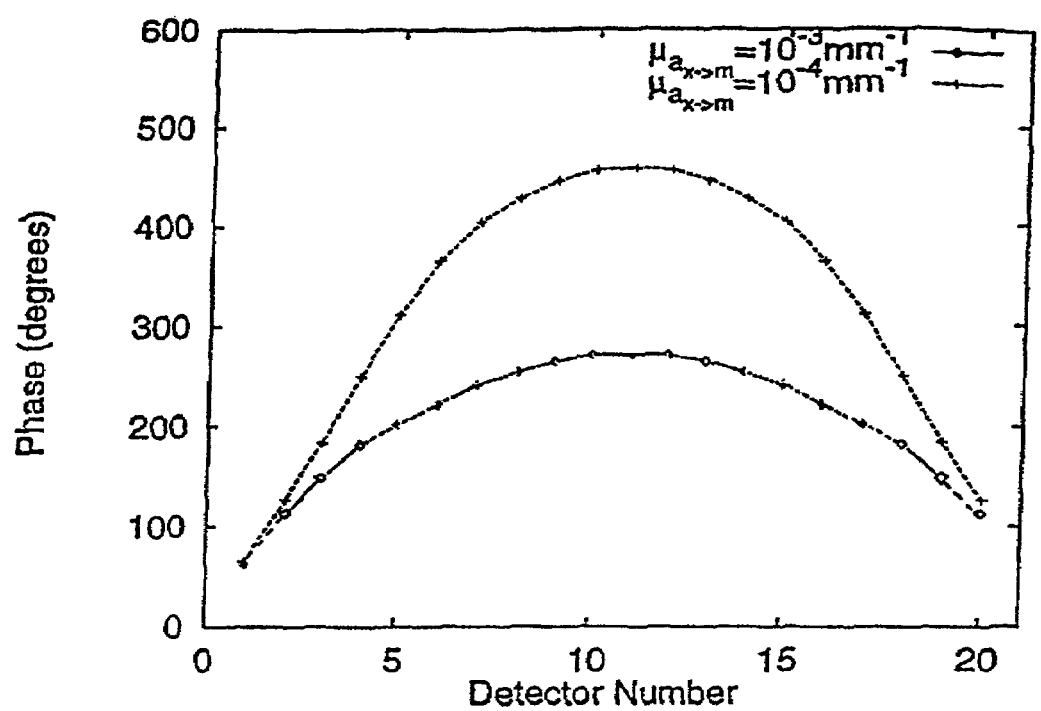

In order to evaluate the influence of $\eta\mu_{a_{x \to m}}$, $\theta_m$ and $M_m$ were computed at each detection site D1-D20 as the value of $\eta\mu_{a_{x \to m}}$ in the heterogeneity increased from $10^{-4}$ mm$^{-1}$ to $10^{-1}$ mm$^{-1}$ and as $\eta\mu_{a_{x \to m}}$ in the background 303 was maintained constant. The lifetime, $\tau$, was set equal to 1 ns for both the object and the background causing contrast due to differences in $\eta\mu_{a_{x \to m}}$. The plots of $\theta_m$ and $M_m$ are shown in FIGS. 4 and 5 respectively for one active source S1. As $\eta\mu_{a_{x \to m}}$ of heterogeneity 102 increases to higher values, the AC intensity approaches an upper limit similar to what is expected in dilute non-scattering solutions. FIG. 5 shows how the fluorescent phase-shift, $\theta_m$, decreases as the absorption coefficient due to the fluorophore, $\mu_{a_{x \to m}}$ is decreased 10 to 100 times the background. From these simulations, $M_m$ appears to be directly dependent upon changes in $\eta\mu_{a_{x \to m}}$ of a simulated tissue heterogeneity 102 whereas $\theta_m$ is indirectly dependent on $\eta\mu_{a_{x \to m}}$ due to changes in photon migration.

Figure 6:
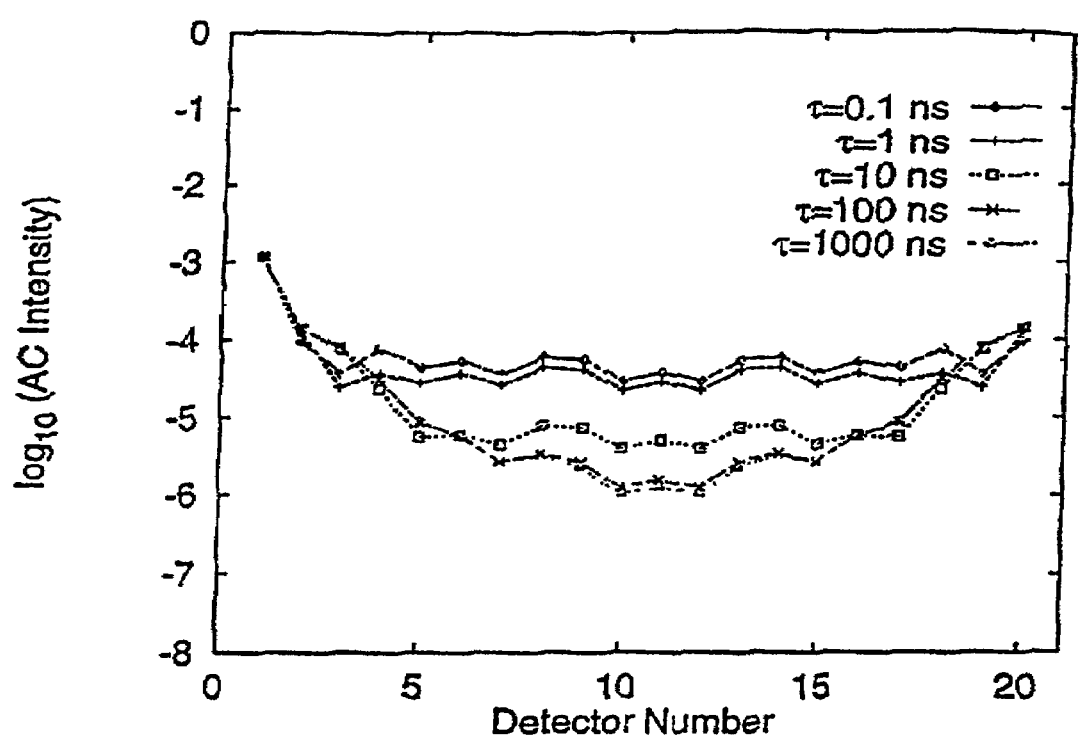
Figure 7:
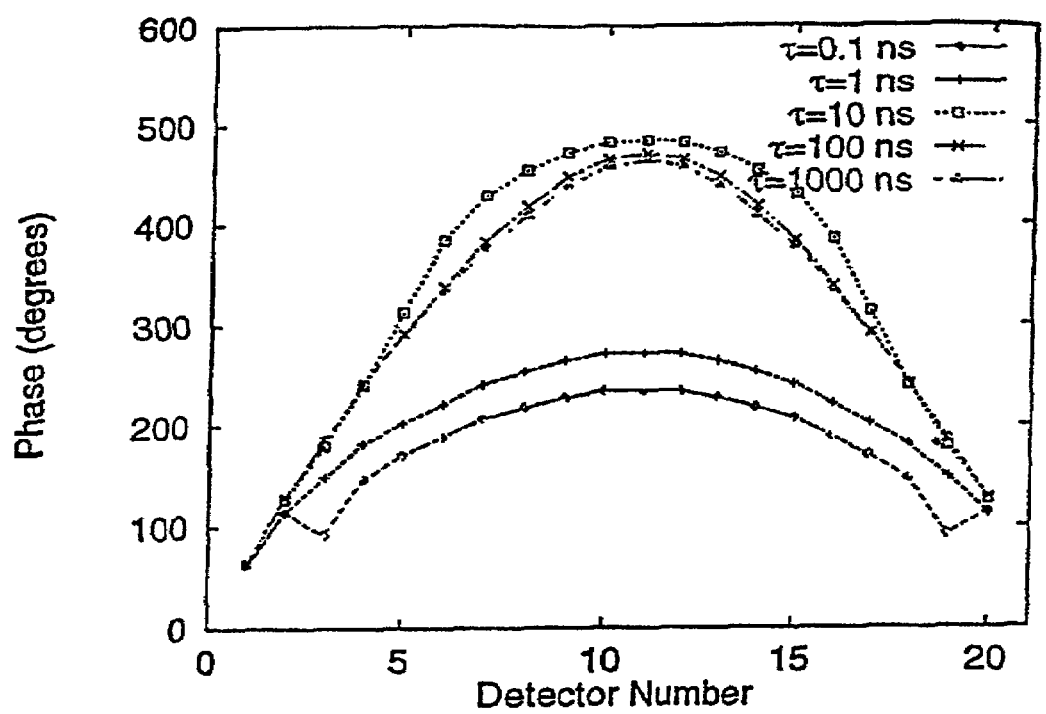

In order to evaluate the influence of $\tau$, $\theta_m$, and $M_m$ were calculated at each detection site D1-D20 as the values of $\tau$ in the heterogeneity varied from $10^{-1}$ ns to $10^3$ ns and the value of $\tau$ in the background was held at 1 ns. The background $\eta\mu_{a_{x \to m}}$ was set to $10^{-5}$ mm$^{-1}$ and $\eta\mu_{a_{x \to m}}$ for the heterogeneity was set to $10^{-3}$ mm$^{-1}$. As shown in FIG. 6, the detected AC intensity increases as $\tau$ decreases. FIG. 7 illustrates the values of the fluorescent phase-shift at each detection site as the lifetime of the heterogeneity is changed from 0.1 ns to 1000 ns. At a given modulation frequency (150 MHz in this calculation), $\theta_m$ first increases, reaches a maximum and then subsequently decreases as $\tau$ is increased from 0.1 ns to 1000 ns. Therefore, both $\theta_m$ and $M_m$ at each detection site D1-D20 appear to be directly influenced by the value of lifetime in the heterogeneity.

Referring back to FIG. 2, in stage 240, the calculated emission phase and intensity, $(\theta_m)_i$ and $(M_m)_i$, are compared to the measured emission phase and intensity, $(\theta_{obs})_i$ and $(M_{obs})_i$, for each detection site "i" to identify a difference or "error" between the measured and calculated values. Because $(\eta\mu_{a_{x\to m}})_j$ impacts $(M_m)_i$, this comparison is posed in the form of the merit function $\chi_\mu^2$ of equation (5) as follows:

$$\chi_\mu^2 = (1/Sk)\sum_{k=1}^{Sk}(1/Di)\sum_{i=1}^{Di}[((M_{obs})_i - (M_m)_i)/\sigma_M]^2 \quad (5)$$

where $\sigma_M$ is the typical standard deviation of noise in $M_m$, taken to be 0.01; Sk=number of excitation source sites indexed by k; and Di=number of detection sites indexed by i. The goal of the algorithm is to minimize $\chi_\mu^2$ by appropriate updates of $(\eta\mu_{a_{x\to m}})j$. After an initial update of $(\eta\mu_{a_{x\to m}})j$ another merit function in terms of $(\tau)_j$ participates in the comparison of stage 240. This merit function, $\chi_\tau^2$, is presented as equation (6) as follows:

$$\chi_\tau^2 = (1/Sk)\sum_{k=1}^{Sk}(1/Di)\sum_{i=1}^{Di}[((M_{obs})_i - (M_m)_i)/\sigma_M]^2 + \quad (6)$$

$$[((\theta_{obs})_i - (\theta_m)_i)/\sigma_\theta]^2$$

where $\sigma_\theta$ is the typical standard deviation of noise in $(\theta_m)_i$, taken to be 1 degree; Sk=number of excitation source sites indexed to k; and Di=number of detection sites indexed to i. Since the lifetime influences both $(\theta_m)_i$ and $(M_m)_i$, the phase and AC intensity are used in equation (6).

After the comparison of stage 240 is performed by calculating the merit functions $\chi_\mu^2$ and $\chi_\tau^2$ control flows to conditional 250 to test whether the comparison of the observed values, $(\theta_{obs})_i$ and $(M_{obs})_i$, to the calculated values $(\theta_m)_i$ and $(M_m)_i$ via the merit functions meets a selected convergence criteria. This criteria corresponds to the degree of tolerable error in determining the yield and lifetime values. For one embodiment, convergence is achieved when any of the following three quantities, (i) $\chi^2$, (ii) change in $\chi^2$ in successive iterations of loop 220, or (iii) relative change in $\chi^2$ in successive iterations of loop 220 is less than a predetermined threshold value of $1.0\times10^{-5}$. In other embodiments a different comparison calculation and associated conditional may be employed as would occur to one skilled in the art. If conditional 250 is satisfied, control flows to stage 270 and loop 220 is exited; however, if the criteria is not satisfied, execution of loop 220 continues in stage 260.

In stage 260, the yield, $(y)_j=(\eta\mu_{a_{x\to m}})_j$, and lifetime, $(\tau)_j$, for each grid point j is updated so that these values may reach the minimum error corresponding to the comparison stage 240 and conditional 250 test. In order to update these values, Jacobian matrices are used which describe the sensitivity of the response at each detection position i to changes in $(y)_j=(\eta\mu_{a_{x\to m}})_j$, and lifetime, $(\tau)_j$, at each grid point, j. Three Jacobian matrices are employed:

$$\overline{J}(M,\eta\mu_{a_{x\to m}}); \overline{J}(M,\tau); \overline{J}(\theta,\tau);$$

where, the elements Ji,j of these Jacobian matrices are given by Ji,j=$[\partial M_i/(\partial(\eta\mu_{a_{x\to m}})_j]$; Ji,j=$[\partial M_i/\partial\tau_j]$; and Ji,j=$[\partial\theta/\partial\tau_j]$, respectively. These elements may be calculated by solving the diffusion (1) and (2) four times for each grid point, j to obtain $M_{m,i}$ and $\theta_{m,i}$ calculated with $(\tau)_j$ and $(\tau+\partial\tau)_j$ and with $(\eta\mu_{a_{x\to m}})_j$ and $(\eta\mu_{a_{x\to m}}+\partial\eta\mu_{a_{x\to m}})_j$. From least squares minimization, the update to yield and lifetime is calculated. In one preferred embodiment, this updating algorithm is adapted from an algorithm used to reconstruct images obtained by electrical impedance tomography like the algorithm suggested by Yorkey, et al., *Comparing reconstruction Algorithms for Electrical Impedance Tomography*, 34 Transactions in Biomedical Engineering pp. 843-52 (1987). The Jacobian Matrices are used to solve for update vectors, $[\overline{\Delta\eta\mu_{a_{x\to m}}}]$ and $[\overline{\Delta\tau}]$ to estimated yield and lifetime vectors, $[\overline{\eta\mu_{a_{x\to m}}}]$ and $[\overline{\tau}]$, respectively. These vectors are of a dimension corresponding to the number of grid points. At each iteration through loop 220, the following Jacobian equations (7) and (8) are solved to determine the update for the estimated yield and lifetime vectors:

$$\left[\frac{\overline{J}(M,\eta\mu_{a_{x\to m}})^T \overline{J}(M,\eta\mu_{a_{x\to m}})}{\sigma_M^2} + \lambda_1\overline{I}\right]\left[\overline{\Delta\eta\mu_{a_{x\to m}}}\right] = \quad (7)$$

$$\left[\frac{\overline{J}(M,\eta\mu_{a_{x\to m}})^T}{\sigma_M^2}(\overline{M}_{m_{obs}} - \overline{M}_m)\right]$$

$$\left[\frac{\overline{J}(M,\tau)^T \overline{J}(M,\tau)}{\sigma_M^2} + \frac{\overline{J}(\theta,\tau)^T \overline{J}(\theta,\tau)}{\sigma_\theta^2} + \lambda_2\overline{I}\right]\left[\overline{\Delta\tau}\right] = \quad (8)$$

$$\left[\frac{\overline{J}(M,\tau)^T}{\sigma_M^2}(\overline{M}_{m_{obs}} - \overline{M}_m) + \frac{\overline{J}(\theta,\tau)^T}{\sigma_\theta^2}(\overline{\theta}_{m_{obs}} - \overline{\theta}_m)\right]$$

$\overline{M}_{m_{obs}}$ and $\overline{M}_m$ are the observed and calculated vectors of the log of AC intensity at each of the i detection sites, respectively. $\overline{\theta}_{m_{obs}}$ and $\overline{\theta}_m$ are the observed and calculated vectors of the phase lag at each of the i detection sites, respectively. Due to the ill-conditioned nature of the Jacobian matrices, the terms $\lambda_1 I$ or $\lambda_2 I$ are added as part of a Marquardt minimization scheme where I is an identity matrix. The parameters $\lambda_1$ or $\lambda_2$ are adjusted via a Maquardt-Levenberg type algorithm of the type disclosed in Press et al., *Numerical Recipes: The Art of Scientific Computing*, (Cambridge University Press, 1992). Conventional numerical methods are employed to solve the simultaneous linear algebraic equations resulting from the Jacobian matrix equations (7) and (8). The Jacobian matrices are re-calculated at each iteration through loop 220. It has been found that equations (7) and (8) provide a way to select appropriate changes to the yield and lifetime estimates; however, other numerical approaches to recursively iterate to acceptable estimates as would occur to one skilled in the art are also contemplated. Once the update is complete, control returns to stage 230.

If the convergence criteria is satisfied in conditional 250, then estimation of yield and lifetime for the grid points has reached an acceptable minimum and control flows to stage 270. In stage 270 an image signal is generated by processor 160 from the spatial variation of the yield and/or lifetime fluorescence characteristics. This image signal is sent to output device 164, which displays an image in response.

Because the fluorescence characteristics of yield and lifetime typically vary with the biologic environment of the fluorophore, this image is generally indicative of tissue variation and offers the capability to detect heterogeneities 102, 103. For example, laser diodes capable of supplying Near infrared (NIR) light that can penetrate tissue several centimeters, and fluorescent contrast agents responsive to NIR light may be used to provide a viable imaging system. In one embodiment, this to system is adapted for use with an endoscope.

Besides yield and lifetime, the spatial variation of other fluorescence characteristics useful to distinguish diseased tissues may be mapped using the diffusion equations (1) and (2). Such alternative fluorescence characteristics include, but are not limited to, quantum efficiency $\eta$ and/or fluorescent absorption coefficient $\mu_{a_{x \to \eta}}$ determined as separate properties independent of the yield product.

It should be appreciated that imaging in accordance with the present invention, such as process 210, includes exposing biologic tissue at the tissue-air interface to an excitation light and detecting the light which has propagated to a detector located some distance away from the source on the air-tissue interface. The time-dependent propagation characteristics of multiply scattered light emitted in response to this exposure are measured. As described in connection with process 210, an intensity-modulated light source may be employed for frequency-domain measurements. The propagating wave of intensity-modulated light is amplitude attenuated and phase-shifted relative to the excitation light owing to the spatial distribution of fluorescence properties. From exterior measurements of phase-delay and amplitude modulation, interior fluorescence properties are determined using a mathematical relationship that models the multiple light scattering behavior of the tissue, such as the diffusion equations (1) and (2). These fluorescence properties may be mapped to provide a corresponding interior image of the tissue, facilitating the identification of hidden heterogeneities.

In an alternative embodiment, measurements may be made in the time domain. For this embodiment, a pulse of light may be launched at the air-tissue interface, which is broadened during its propagation in tissues due to the spatial variation of fluorescence properties within the tissue. The broadened pulse emitted from the air-tissue interface is measured. For this embodiment, the diffusion equation in the time-domain form, or such other mathematical relationship characterizing multiply scattered light propagation through the tissue may be utilized to calculate the fluorescence characteristics as would occur to those skilled in the art. These characteristics may then be mapped to generate a corresponding image in the manner described in connection with process 210.

Both the frequency and time domain approaches account for the time propagation of light through the tissue due to multiple scattering events. For a given photon, the travel time through a multiple scattering media increases with the number of collisions or "scattering events", which corresponds to a longer scattering path. This travel time is known as the "time-of-flight". Typically, time-of-flight is on the order of a fraction of a nanosecond to a few nanoseconds in biologic tissue. For the usual case of many photons each traveling along different scattering paths, a mean "time-of-flight" of the photons may be determined from the frequency or time domain measurements. These time-based measurements are utilized with the corresponding mathematical model to map the fluorescence characteristics.

The fluorescence characteristic map provides an image of tissue that may be based only on intrinsic fluorophores in the tissue or enhanced by introduction of a contrast agent that is selective to tissue volumes of interest. This contrast agent may absorb radiation as in the case of contrast agents for x-ray and CT imaging to provide a corresponding darkening of the image regions for the tissue volumes of interest. Unfortunately, the contrast provided through selective absorption is limited. Accordingly, in another embodiment of the present invention, a technique to select exogenous contrast agents which augment the conventional contrast mechanisms is provided. It has been discovered that fluorescence properties that change with the local biochemical environment often provide greater contrast for reconstruction of diseased tissue volumes that can be afforded by absorption-based contrast alone. Among the properties that offer this local environment contrast mechanism, are fluorescence lifetime $\tau$, i.e., the mean time between the absorption of an excitation photon and the emission of a fluorescent photon; fluorescence quantum efficiency $\eta$, i.e., the number of fluorescent photons emitted per excitation photon absorbed; and fluorescence quantum yield y.

It has been discovered that fluorophore contrast agents having a fluorescence lifetime within an order of magnitude—or factor of ten (10)—of photon "time-of-flights" of the tissue being interrogated are surprisingly advantageous in providing contrast for photon migration imaging. One way of utilizing this surprising advantage is to select an agent with a fluorescence lifetime within a factor of ten (10) of the mean time-of-flight predicted for the tissue to be imaged. Typically, by applying this principle, a preferred range for the contrast agent lifetime of about 0.1 to 10 ns results. More preferably, the range for the fluorescence lifetime of the contrast agent is within a range of about 0.5 to 5 ns. A still more preferred range for fluorescence lifetime of the agent is about 0.2 to about 2 ns. A most preferred value for the lifetime is about 1 ns.

It has also been discovered that fluorescence characteristics may influence the resolution of measurements of the detected light emission. For example, in the frequency domain, it has been found that the amplitude of the intensity-modulated fluorescent light emanating from a hidden heterogeneity containing the agent generally increases with quantum yield y or quantum efficiency $\eta$. Further, as fluorescence lifetime $\tau$ within the heterogeneity increases relative to its surroundings, the phase contrast increases. Conversely, the amplitude of the detected intensity-modulated light decreases with increasing fluorescence lifetime $\tau$ within the heterogeneity relative to its surroundings. Through these discoveries, a fluorescent agent may be selected or formulated to provide a desired measurement resolution and fluorescence lifetime contrast suitable for photon migration interrogation of a heterogeneous arrangement of tissue. These discoveries are further described in connection with Examples 4-7 at the end of this description.

Generally, as Examples 4-7 illustrate, the selection or formulation of a suitable contrast agent is performed by determining the relationship between image contrast and fluorescent properties such as lifetime, yield, or quantum efficiency a function of the location of a heterogeneity selective to the given contrast agent. These relationships may be evaluated for a number of different agents to select a preferred agent for a given contrast problem. For frequency domain based evaluation, image contrast may be characterized in terms of phase shift variation, modulation variation, or both. Furthermore, the image contrast may be enhanced by measuring the response of a sample to a first excitation light without the agent to provide a baseline (the "absence" case), and then measuring the response to a second excitation light after introduction of the agent (the "presence" case). Data corresponding to these two responses is compared to evaluate the contrast capability of agent. The first excitation light wavelength may be selected to stimulate intrinsic fluorescent response of the tissue at the same wavelength expected to stimulate agent fluorescence. Alternatively, the first excitation light wavelength may be the same as for the fluorescent light emitted by the agent to enhance separation of intrinsic tissue fluorescence from fluorescence of the agent. Also, multiple comparisons may be performed using different wavelengths to better evaluate the influence of the contrast agent.

In another embodiment of the present invention, the photon fluence equation and Jacobian estimation process is adapted to determine a map of a designated fluorophore uptake concentration. For this embodiment, a first map of chromophore adsorption coefficients $\mu_{a_x \to c}$ and scattering coefficients $\mu'_s$ are determined in the absence of the designated fluorophore by estimating the chromophore adsorption coefficient $\mu_{a_x \to c}$ and scattering coefficient $\mu'_s$ at each grid point j in place of the yield and lifetime estimates. Diffusion equation (1) for $\Phi_x(r, \omega)$ may be used in conjunction with modified Jacobian equations (7) and (8) to create this first map. The modification substitutes the chromophore adsorption and scattering coefficients in place of the yield and after adaptation to accommodate these new characteristics as follows:

$$\left[\frac{\overline{J}(M_x, \mu_{a_x \to c})^T \overline{J}(M_x, \mu_{a_x \to c})}{\sigma_M^2} + \frac{\overline{J}(\theta_x, \mu_{a_x \to c})^T \overline{J}(\theta_x, \mu_{a_x \to c})}{\sigma_\theta^2} + \lambda_2 \overline{I}\right][\Delta \mu_{a_x \to c}] = \quad (9)$$

$$\left[\frac{\overline{J}(M_x, \mu_{a_x \to c})^T}{\sigma_M^2}(\overline{M}_{x_{obs}} - \overline{M}_x) + \frac{\overline{J}(\theta_x, \mu_{a_x \to c})^T}{\sigma_\theta^2}(\overline{\theta}_{x_{obs}} - \overline{\theta}_x)\right]$$

and $$\left[\frac{\overline{J}(M_x, \mu_s)^T \overline{J}(M_x, \mu_s)}{\sigma_M^2} + \frac{\overline{J}(\theta_x, \mu_s)^T \overline{J}(\theta_x, \mu_s)}{\sigma_\theta^2} + \lambda_2 \overline{I}\right][\Delta \mu_s] = \quad (10)$$

$$\left[\frac{\overline{J}(M_x, \mu_s)^T}{\sigma_M^2}(\overline{M}_{x_{obs}} - \overline{M}_x) + \frac{\overline{J}(\theta_x, \mu_s)^T}{\sigma_\theta^2}(\overline{\theta}_{x_{obs}} - \overline{\theta}_x)\right]$$

The elements of the four Jacobian matrices employed, $\overline{J}(M_x, \mu_{a_x \to c})$, $\overline{J}(M_x, \mu_s)$, $\overline{J}(\theta_x, \mu_{a_x \to c})$, and $\overline{J}(\theta_x, \mu_s)$ are given by $$j_{i,j} = \frac{\partial M_{x_i}}{\partial (\mu_{a_x \to c})_j}, \ j_{i,j} = \frac{\partial M_{x_i}}{\partial \mu_{sj}}, \ j_{i,j} = \frac{\partial \theta_{x_i}}{\partial (\mu_s)_j} \text{ and } j_{i,j} = \frac{\partial \theta_{x_i}}{\partial (\mu_{a_x \to c})_j}$$

respectively. Updates to the absorption and scattering map were conducted to minimize the merit function $\chi^2$:

$$\chi^2 = \frac{1}{n_s} \sum_{k=1}^{n_s} \frac{1}{n_d} \sum_{i=1}^{n_d} \left(\frac{M_{xobs,i} - M_{x,i}}{\sigma_M}\right)^2 + \left(\frac{\theta_{xobs,i} - \theta_{x,i}}{\sigma_\theta}\right)^2 \quad (11)$$

where $n_s$=Sk and $n_d$=Di.

After generating the first map, the designated fluorescent contrast agent is introduced, and the total adsorption coefficient $\mu_{a_x}$ is determined by substituting $\mu_{a_x}$ in place of $\mu_{a_x \to c}$ in equations (9)-(11) to obtain a second map of the total adsorption coefficient. Noting that $\mu_{a_x} = \mu_{a_x \to m} + \mu_{a_x \to c}$, and that the uptake of the fluorescing contrast agent is directly proportional to $\mu_{a_x \to m}$, uptake concentration may be mapped by determining a difference between the adsorption coefficient variations for the first and second maps. This "difference map" may then be used to generate an image corresponding to the uptake concentration.

Another alternative embodiment measures the emission responsive to each of a number of light source modulation frequencies f. The total number of different frequencies employed is designated Mf. To obtain this additional data, an iteration of loop 220 is performed for each frequency f indexed to m. The number of sources, Sk and detection sites Di are indexed to k and i, respectively. This additional data may be used to enhance imaging results obtained with system 110 or to permit reduction of the number of detection sites or excitation source sites in the evaluation. A representative merit function corresponding to this additional data is given in equation (12) as follows:

$$\chi_T^2 = (1/Mf) \sum_{m=1}^{Mf} (1/Sk) \sum_{k=1}^{Sk} (1/Di) \quad (12)$$

$$\sum_{i=1}^{Di} [(((M_{obs})_i - (M_m)_i / \sigma_M)]^2 + [((\theta_{obs})_i - (\theta_m)_i)/\sigma_\theta]^2$$

Besides fluorescence yield and lifetime, the multi-frequency method can be employed to map other optical characteristics of interest. Besides a sinusoidally modulated light source, the present invention may be adapted to operate with a pulsed or other time-varying excitation light source in alternative embodiments.

Figure 15:
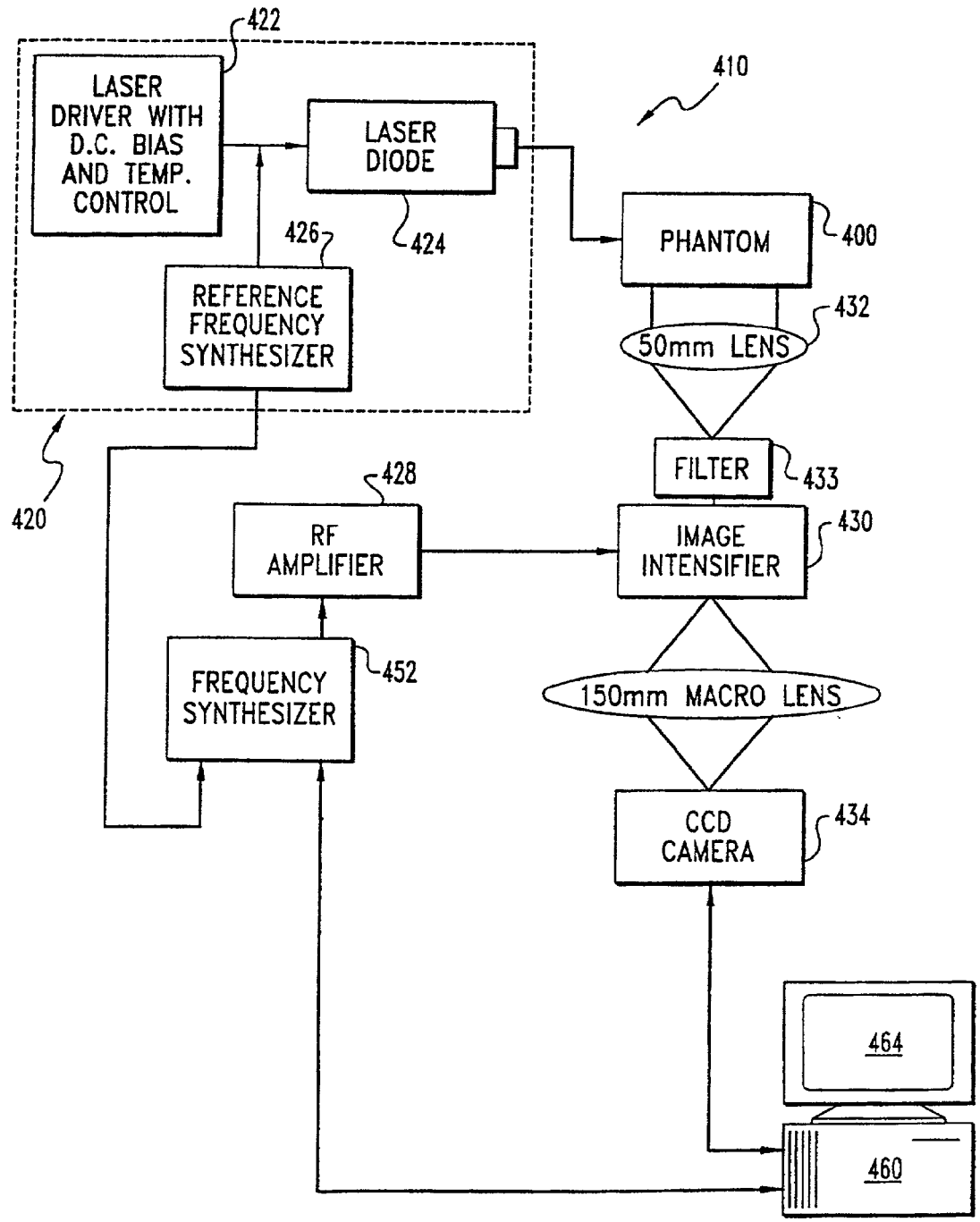
FIG. 15 is a schematic illustration of a system of an alternative embodiment of the present invention.

FIG. 15 depicts an optical system 410 of another embodiment of the present invention. This system includes modulated light source 420 with laser driver 422, operatively coupled laser diode 424, and reference frequency generator 426. Source 420 is configured to deliver modulated light to tissue phantom 400, and the emitted light from the phantom is focused onto a gain modulated image intensifier with 50 mm lens 432 through filter 433. Filter 433 may be a bandpass or low pass arrangement selected to isolate to a selected wavelength. Typically filter 433 is configured to pass at least the anticipated fluorescent emission wavelength and may additionally or alternatively be configured to pass the excitation light wavelength. Intensifier 430 includes a photocathode face, which converts photons to electrons, a Multi-Channel Plate (MCP) which multiplies the electronic signal by avalanche multiplication, and a phosphorescent screen, which converts electrons into an optical image. Preferably, intensifier 430 is a fast intensifier, of the variety manufactured by Litton Electronics, Inc., which enables modulation by applying a DC bias and an RF signal from amplifier 428 between the photocathode and the MCP. For this example, the modulation of the image from intensifier 430 is phase-locked to the laser diode 424 by a 10 MHz output signal from synthesizer 426. By modulating the laser diode 424 and the image intensifier 430 at the same frequency, a steady-state image results on the phosphor screen. U.S. Pat. No. 5,213,105 to Gratton et al. provides additional background concerning certain aspects of this technique. The image from the phosphor screen is focused through interference filter 433 on a Charge Coupled Device (CCD) camera 434 via 150-mm macro lens 436. Camera 434 has a 512×512 array of CCD detectors configured to provide a corresponding pixelated image. Camera 434 is operatively coupled to processor 460 of a similar configuration to processor 160 previously described.

simulation of the process 210. Simulations of this kind, including the simulation of tissue, are an acceptable means of demonstrating fluorescent spectroscopic imaging performance to those skilled in the art. Examples 1-3 use simulated values obtained by solving the diffusion equations (1) and (2) for $\theta_m$ and $M_m$ under the conditions of table 2 as follows:

TABLE 2

| Case | $\mu_{a_{x \to q}}$ (mm$^{-1}$) | $\mu_{a_m}$ (mm$^{-1}$) | $\mu_{s_x}$ or $\mu_{s_m}$ (mm$^{-1}$) | $\tau$ (background) (ns) | $\eta\mu_{a_{x \to m}}$ (background) (mm$^{-1}$) | Gaussian Noise in log of AC intensity $\sigma M$ | Gaussian Noise in phase $\sigma_\theta$ (degrees) |
|---|---|---|---|---|---|---|---|
| 5.1 | 0.0 | 0.0 | 1.0 | 10.0 | $1.0 \times 10^{-5}$ | 0.01 | 0.1 |
| 5.2 | $1.0 \times 10^{-3}$ | 0.0 | 1.0 | 10.0 | $1.0 \times 10^{-5}$ | 0.01 | 0.1 |
| 5.3 | 0.0 | 0.0 | 1.0 | 10.0 | $1.0 \times 10^{-5}$ | 0.01 | 1.0 |

Following each acquired image, a phase delay between the image intensifier 430 and the laser diode 424 is induced by stepping the phase of the image intensifier 430 to values between 0 and 360 degrees with the frequency synthesizer 452 under the control of processor 460. Since the gain modulation of image intensifier 430 and laser diode 424 occurs at the same frequency, homodyning results in a steady phosphorescent image on intensifier 430, which is dependent upon phase. Preferably, control between synthesizer 452 and processor 460 is obtained by a conventional GPIB interface. Images from the phosphorescent screen of the image intensifier 430 are then gathered at each phase delay. The incremental phase delayed images are then used to generate a map of phase-shift and intensity modulation ratio between the excitation and emitted light from phantom 400. By applying interference or appropriate optical filters, the emission light may be selectively separated from the excitation light and measured. Camera 434 output may be processed by processor 460 using process 210.

In other embodiments, a wide area illumination source is preferred to provide a larger, more uniform front illumination in a reflective geometry. This illumination approach facilitates faster imaging of multiple sights and a more natural physical correlation between photon migration images and pathology. Also, a camera which has a tapered fiber optic coupler from the image intensifier to the CCD array is envisioned to increase the efficiency of light coupling from the intensifier to the CCD array and reduce the physical size and weight of the imager.

The present invention will be further described with reference to the following specific Examples 1-8. It will be understood that these examples are illustrative and not restrictive in nature. Examples 1-4 involve the computer The examples simulate tissue phantom 300 of FIG. 3 having a 100 mm diameter. Values of $\theta_m$ and $M_m$ were computed at each of the D1-D20 detection sites of FIG. 3 in response to the 4 modulated light sources S1-S4 located at the periphery. The excitation light modulation frequency f was simulated at 150 MHz. Diffusion equations (1) and (2) were solved to provide 80 simulated values of $\theta_m$ and $M_m$ corresponding to the various combinations of detection and source sites (Sk*Di=4×20=80). Gaussian noise with a standard deviation of 0.1 degrees (or a liberal 1 degree) in $\theta_m$ and 1% in $M_m$ were superimposed on the diffusion equation solutions. Adapted MUDPACK routines were used to solve the diffusion equations (1) and (2) on a SunSparc10 computer. These obtained data sets were used as simulated input data to process 210 for examples 1-3. The results are shown in tables 3 and 4 are as follows:

TABLE 3

| Case | Area, object 1 (mm$^2$) | Location, object 1 (x,y), (mm, mm) | Area, object 2 (mm$^2$) | Location, object 2 (x,y), (mm, mm) |
|---|---|---|---|---|
| 5.1 | 706.0 (expected) 742.2 (obtained) | (60,60) (expected) (60.8,58.5) (obtained) | not applicable | not applicable |
| 5.2 | 706.0 (expected) 703.1 (obtained) | (60,60) (expected) (59.4,58.3) (obtained) | not applicable | not applicable |
| 5.3 | 314.1 (expected) 381.0 (obtained) | (32.3,67.7) (expected) (34.0,67.7) (obtained) | 314.1 (expected) 342.0 (obtained) | (67.7,32.3) (expected) (65.0,35.0) (obtained) |

TABLE 4

| Case | $\eta\mu_{a_{x \to m}}$ (object) (mm$^{-1}$) | $\tau$ (object) (ns) |
|---|---|---|
| 5.1 | $1.0 \times 10^{-3}$ (expected) $0.93 \times 10^{-3}$ (obtained) | 1.0 (expected) 1.03 (obtained) |
| 5.2 | $1.0 \times 10^{-3}$ (expected) $0.8 \times 10^{-3}$ (obtained) | 1.0 (expected) 0.7 (obtained) |
| 5.3 | (top left object): $1.0 \times 10^{-3}$ (expected) $2 \times 10^{-3}$ (obtained) (bottom right object): $2.0 \times 10^{-3}$ (expected) $1.8 \times 10^{-3}$ (obtained) | (top left object): 1.0 (expected) 4.1 (obtained) (bottom right object): 2.0 (expected) 3.5 (obtained) |

EXAMPLE 1

Figure 8:
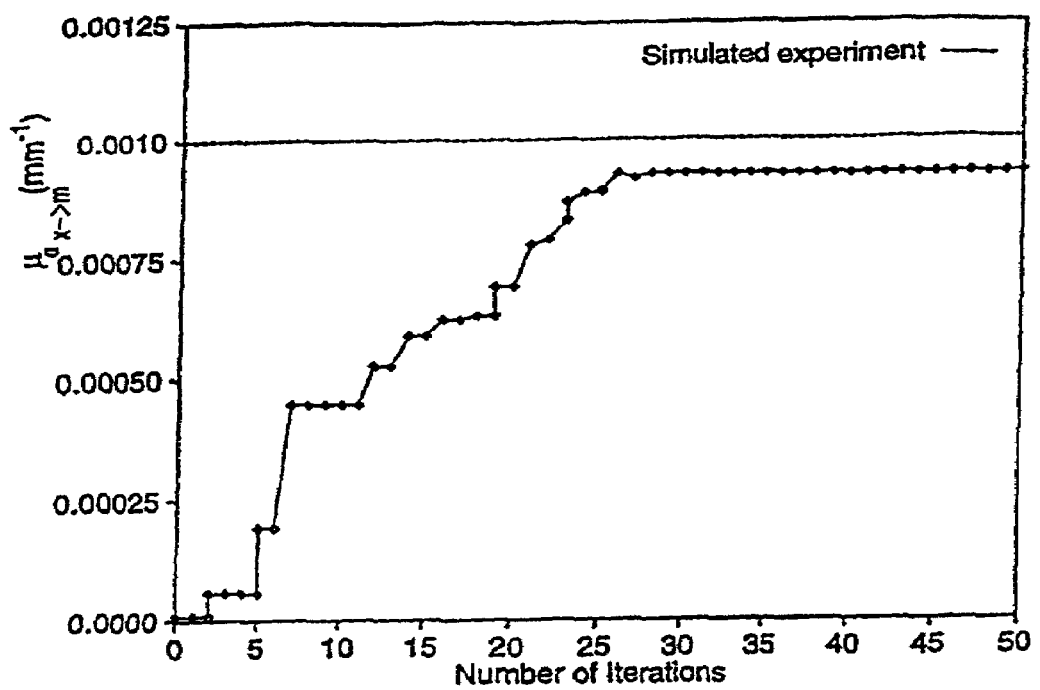
FIGS. 8 and 9 graphically depict convergence of simulated determinations of the spatial variation of fluorescent yield and lifetime, respectively, utilizing one embodiment of the present invention.
Figure 9:
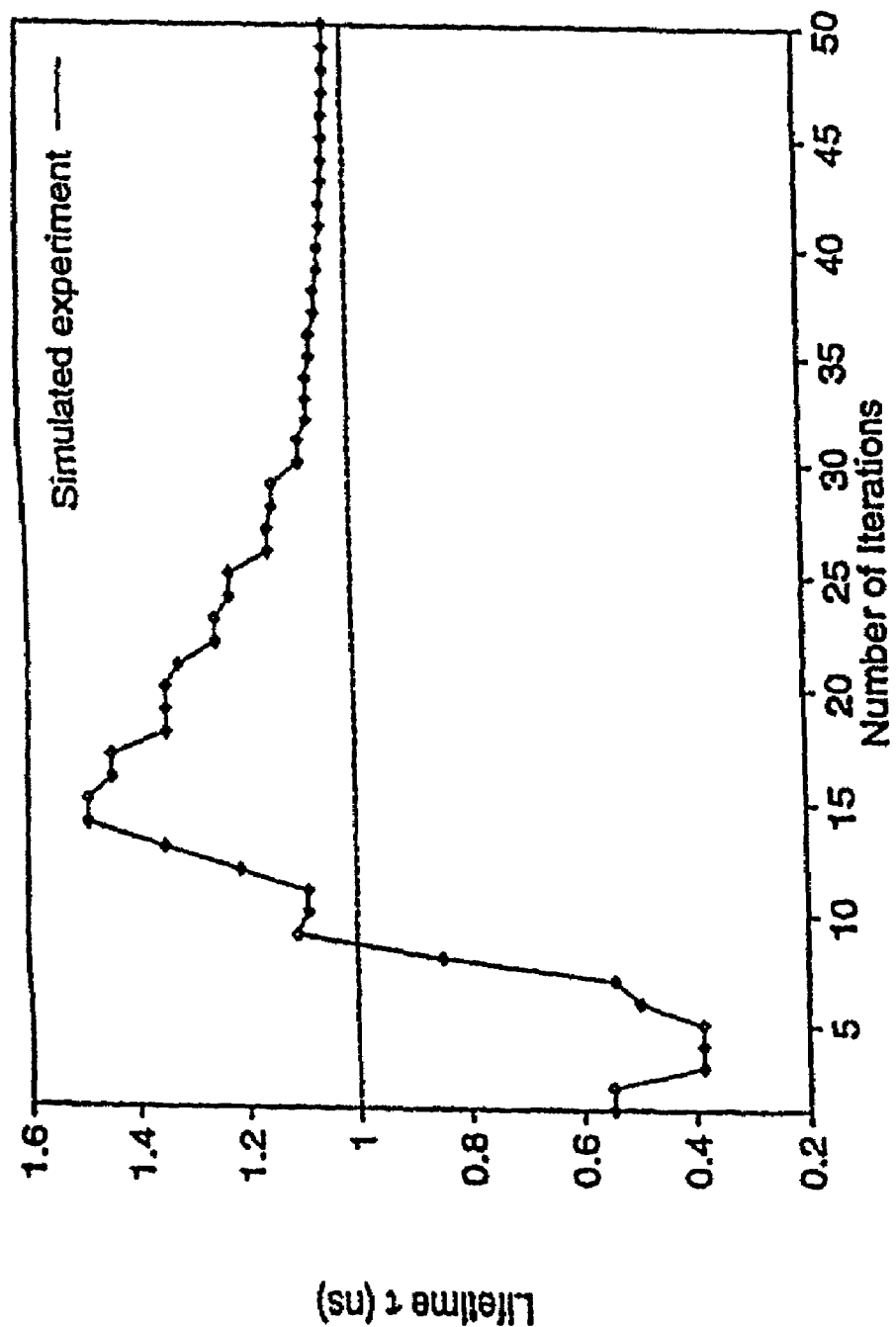
Figure 10:
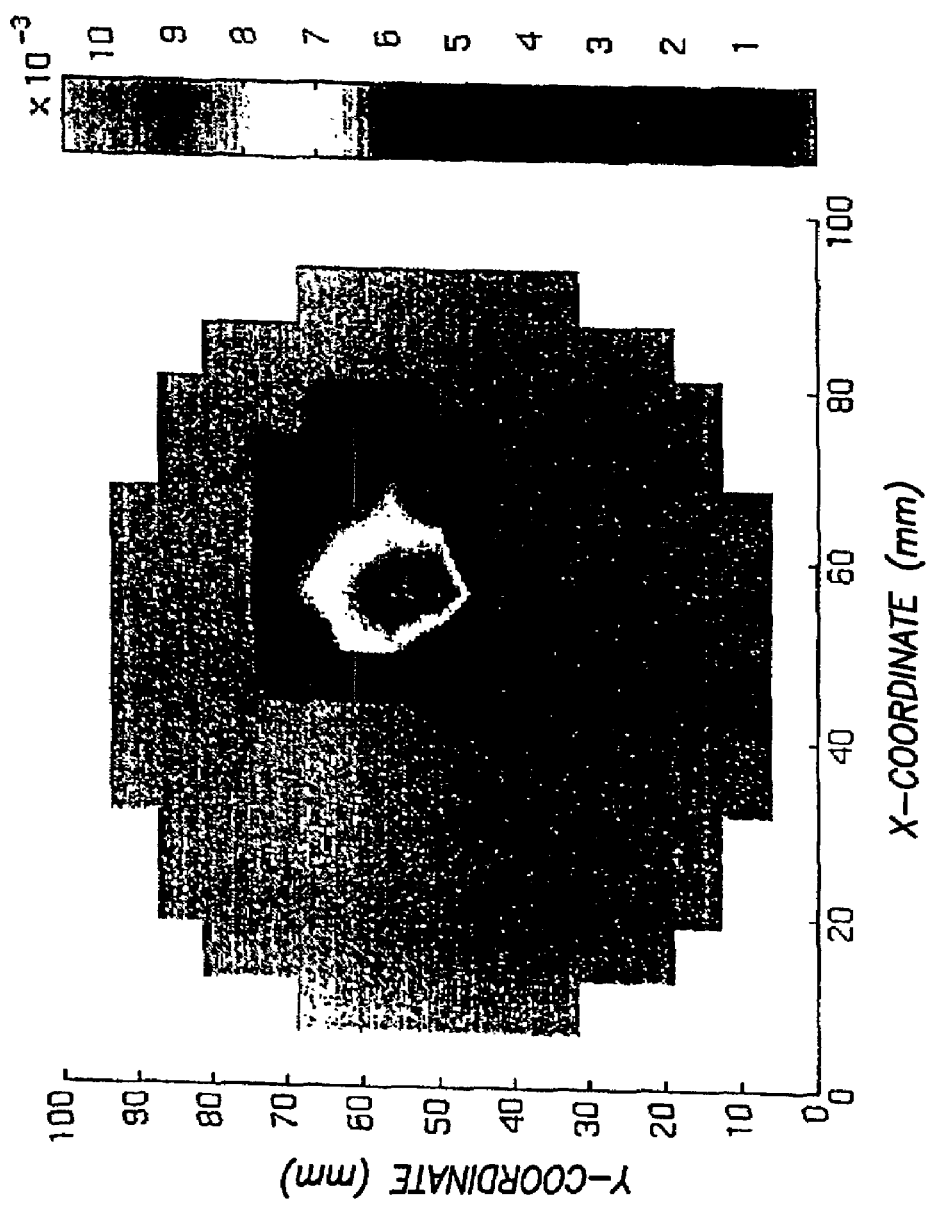
FIGS. 10-14 are computer-generated gray scale images obtained from experimental examples 1-3 of the present invention.
Figure 11:
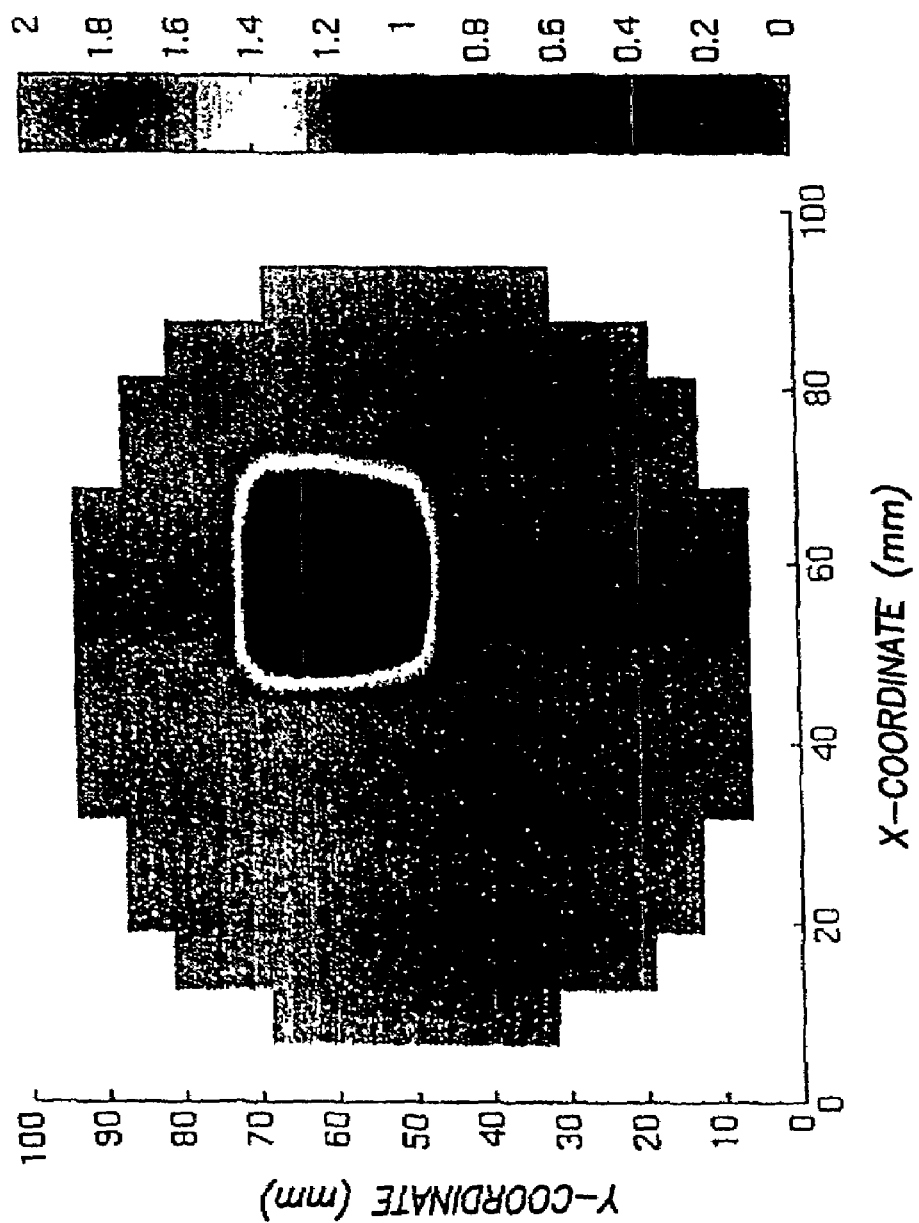

Example 1 reconstructs fluorescent yield and lifetime with no absorption due to non-fluorescing chromophores. To simulate the experimental data for this example, the fluorescent yield, $(\eta\mu_{a_{x\to m}})_j$, for the background and the heterogeneity 302 were chosen as $1\times10^{-5}$ mm$^{-1}$ and $1\times10^{-3}$ mm$^{-1}$ respectively and the fluorescence lifetime, $(\tau)_j$, for the background and the heterogeneity 302 chosen as 10 ns and 1 ns respectively. During the execution of loop 220, no a priori knowledge of either the heterogeneity 302 location or the background-fluorescence properties was assumed and a uniform guess of $1\times10^{-5}$ mm$^{-1}$ and 10 ns was given for the fluorescence yield, $(\eta\mu_{a_{x\to m}})_j$, and lifetime, $(\tau)_j$, respectively. Convergence was achieved in less than 50 iterations of Loop 220 (computational time on a SunSparc10: 2 hours) for a two dimensional 17×17 grid. The average values of $\eta\mu_{a_{x\to m}}$ and $\tau$ in the grid points which occupy the simulated object converge within 50 iterations to $\eta\mu_{a_{x\to m}}=0.93\times10^{-3}$ mm$^{-1}$ and $\tau=1.03$ ns are illustrated in FIGS. 8 and 9, respectively. FIGS. 10 and 11 illustrate the reconstructed images from the mapped values of $\eta\mu_{a_{x\to m}}$ [mm$^{-1}$] and $\tau$ [ns], respectively, and are representative of the expected images. The images were smoothed by interpolation in examples 1-3 to remove spurious points which had unphysically high values, but were surround by values within a physically achievable range. These spurious values were replaced by the average background fluorescence yield and lifetime obtained from simulation of loop 220.

The average values of $\eta\mu_{a_{x\to m}}$ in the grid points which occupy the simulated background converge within 50 iterations to $9\times10^{-5}$ mm$^{-1}$. The value of the background converges to 5.4 ns. The dependence of the final images on the choice of the initial guess was examined by providing an initial uniform guess of $1\times10^{-4}$ mm$^{-1}$ and 10 ns for $(\eta\mu_{a_{x\to m}})_j$, and lifetime, $(\tau)_j$, respectively. This resulted in similar images to those obtained in FIGS. 10 and 11.

The location of heterogeneity 302 was identified as consisting of all the grid points with $\eta\mu_{a_{x\to m}}$ higher than 35% (arbitrarily chosen) of the peak value of the $\eta\mu_{a_{x\to m}}$ (FIG. 10). The average of the coordinates of all the identified object grid points was the position (60.8, 58.5) which is close to position (60, 60) that was used to simulate the experimental data. As listed in Table 3, the area of the heterogeneity based upon our arbitrary definition for identification was 72 mm$^2$, close to that used to generate our simulated experimental data.

EXAMPLE 2

Figure 12:
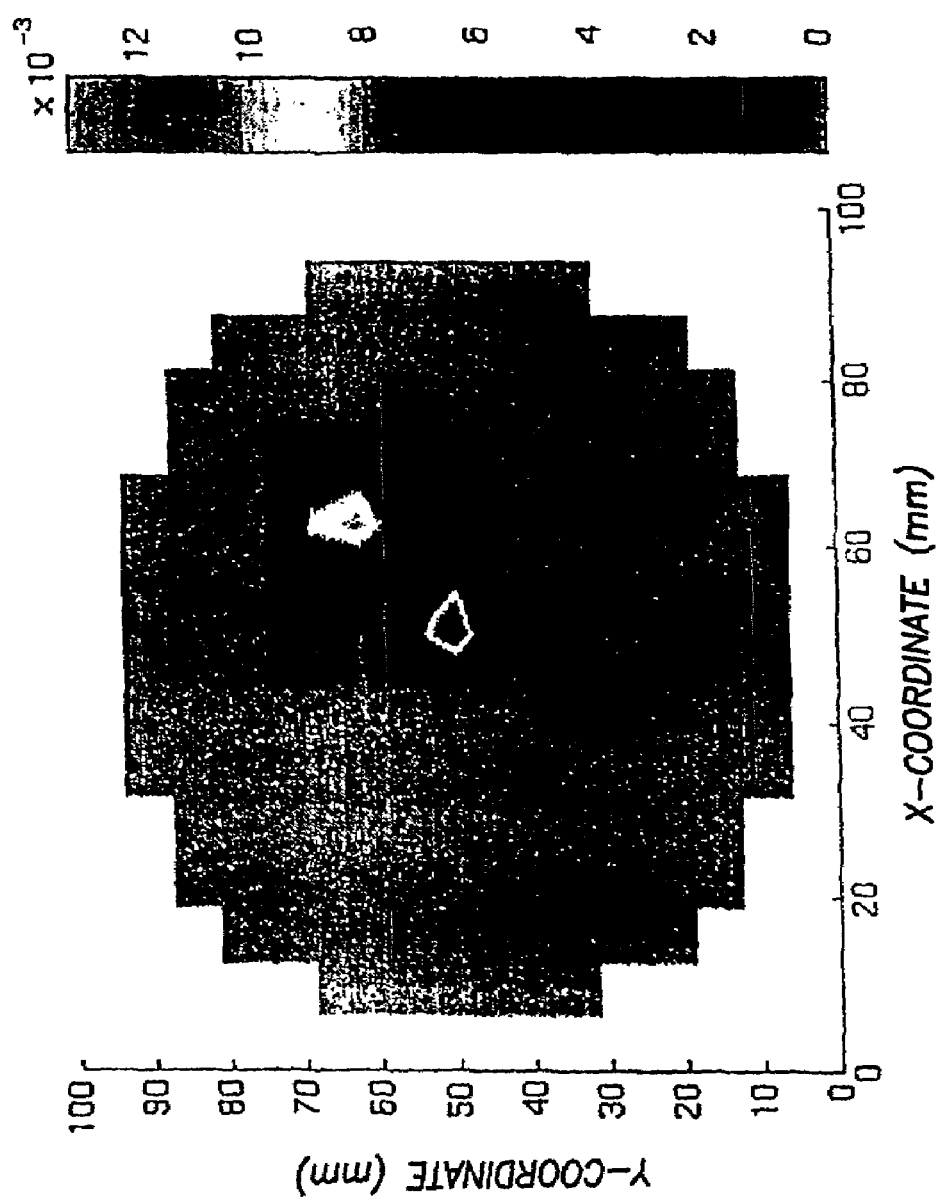
Figure 13:
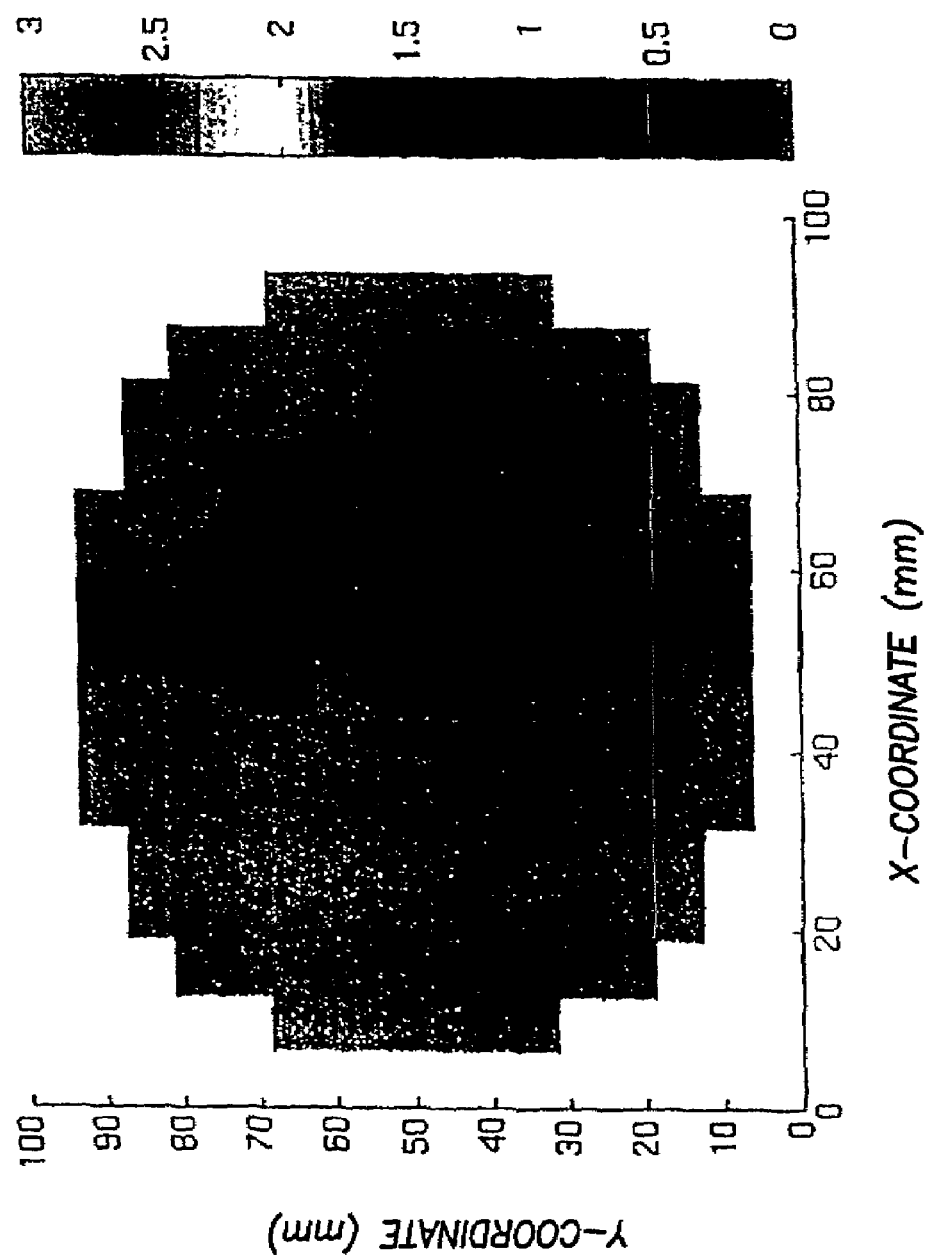

Example 2 reconstructs fluorescent yield and lifetime with a simulated chromophore absorption configured to mimic tissue. The same hidden heterogeneity as well as optical parameters and simulation equipment were used as described in Example 1 except that a uniform background chromophore absorption coefficient, $\mu_{a_x}$, of $1\times10^{-3}$ mm$^{-1}$ was used to generate the simulated experimental data. While excitation light propagation was not employed for image reconstruction, we considered this optical property known to estimate the best possible performance for inverse image reconstruction under physiological conditions. The two-dimensional reconstructed spatial map of the fluorescence yield, $(\eta\mu_{a_{x\to m}})_j$[mm$^{-1}$], and lifetime, $(\tau)_j$[ns], are shown in FIGS. 12 and 13, respectively. As shown in Table 3, the mean value of location of the object according to our criterion based on $\eta\mu_{a_{x\to m}}$ occurred as position (59.4, 58.3) consistent with the conditions used to simulate the experimental data. The dimension of the heterogeneity based upon our arbitrary definition for identification (all grid points with $\eta\mu_{a_{x\to m}}$ higher than 35% of the maximum) were 703 mm$^2$ which is close to that used to generate our simulated experimental data. The average values of $\eta\mu_{a_{x\to m}}$ and $\tau$ in the grid points which occupy the simulated object converge within 50 iterations to the values of $\eta\mu_{a_{x\to m}}=0.8\times10^{-3}$ mm$^{-1}$ and $\tau=0.7$ ns consistent with the values used to generate the simulated experimental data (see Table 3). The average values of $\eta\mu_{a_{x\to m}}$ and $\tau$ in the grid points which occupy the simulated background converge within 50 iterations to values similar to that reported for Example 1.

EXAMPLE 3

Example 3 simulated two hidden heterogeneities in the tissue phantom (not shown in FIG. 3). In this case, the same optical parameters were used as described in example 1 except that the fluorescence yield $\eta\mu_{a_{x\to m}}$ for the objects 1 and 2 was chosen as $1\times10^{-3}$ mm$^{-1}$ and $2\times10^{-3}$ mm$^{-1}$ respectively and lifetime $\tau$ for the heterogeneities chosen as 1 ns and 2 ns, respectively.

Figure 14:
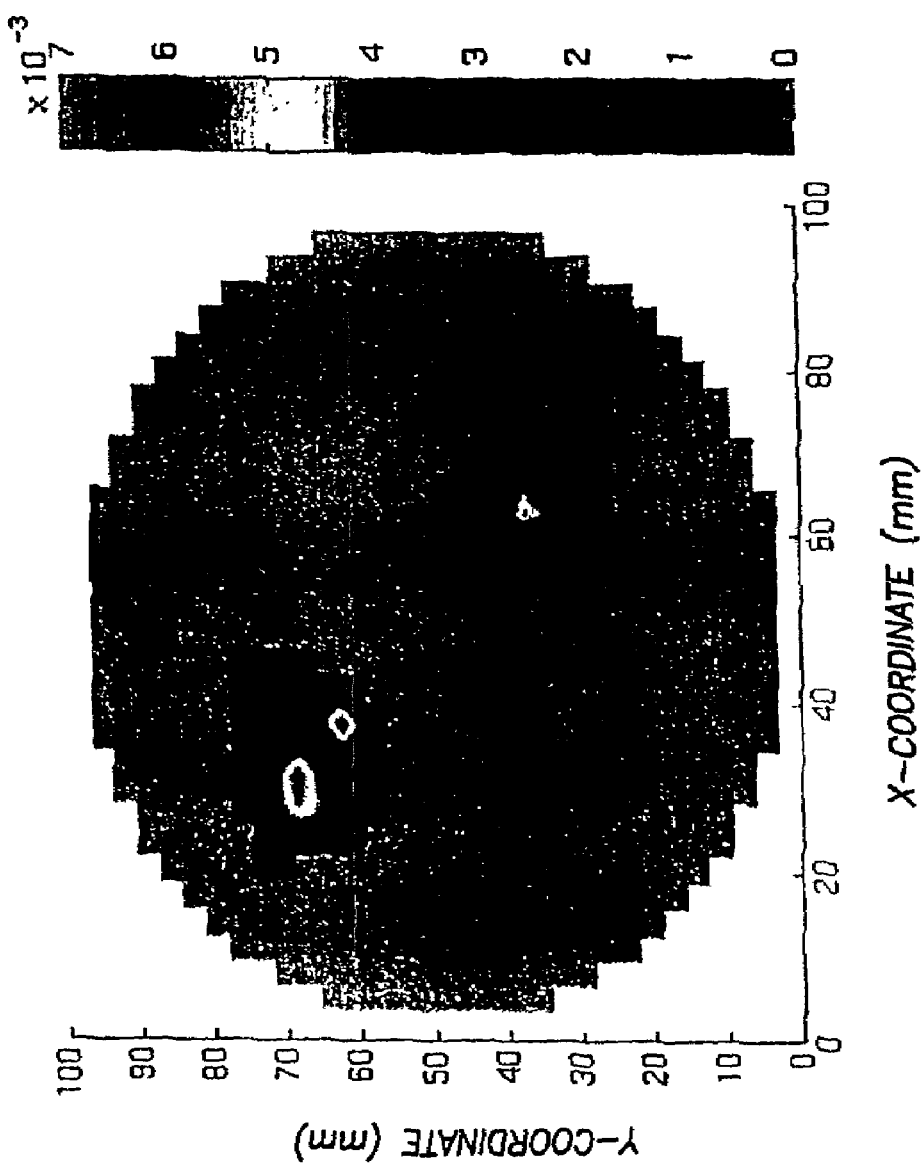

A 33×33 grid was employed instead of a 17×17 grid. An image corresponding to the mapping of yield is depicted in FIG. 14.

EXAMPLE 4

Figure 16:
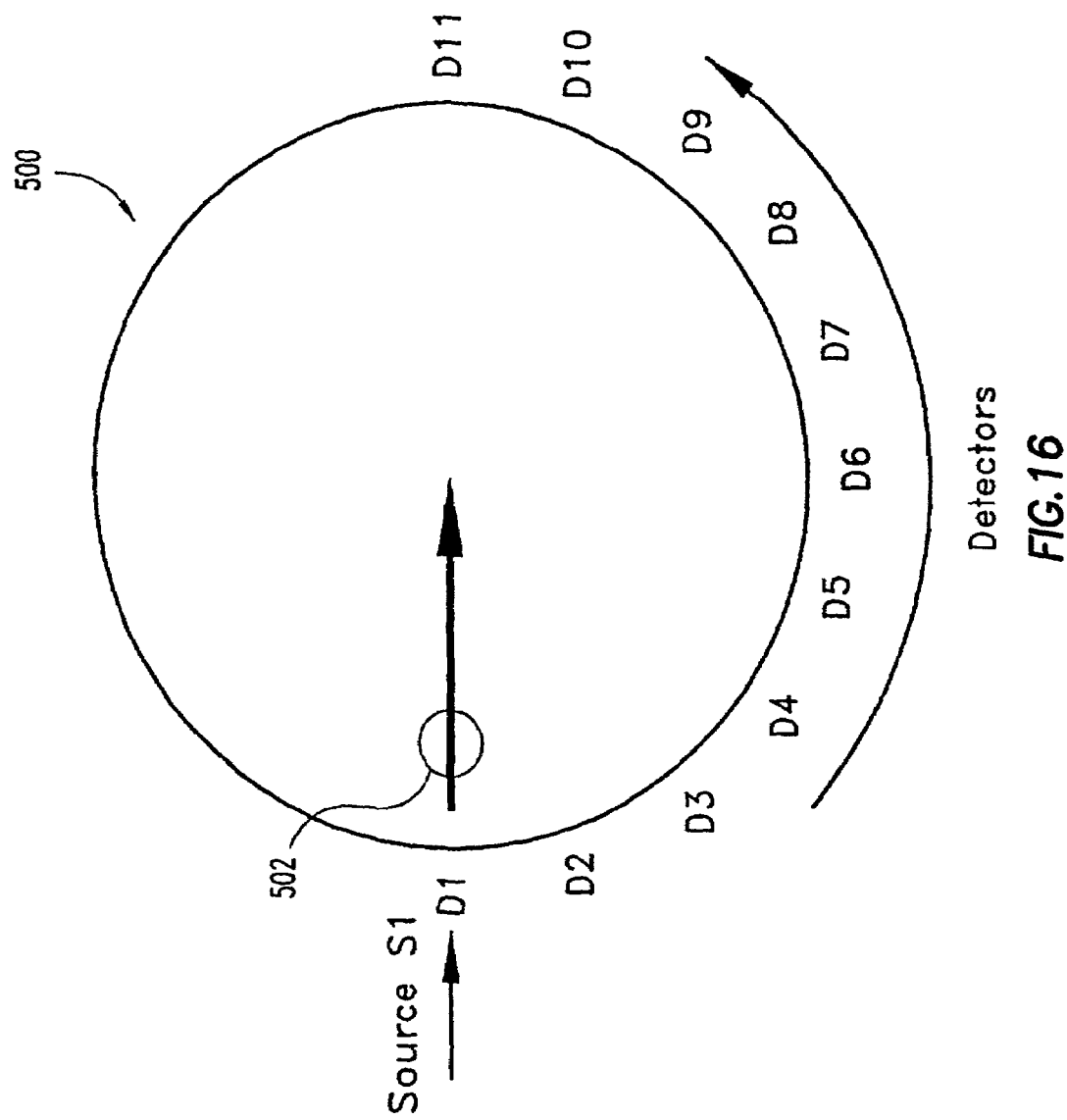
FIG. 16 is a schematic view of another tissue phantom arrangement of the present invention.
Figure 17A:
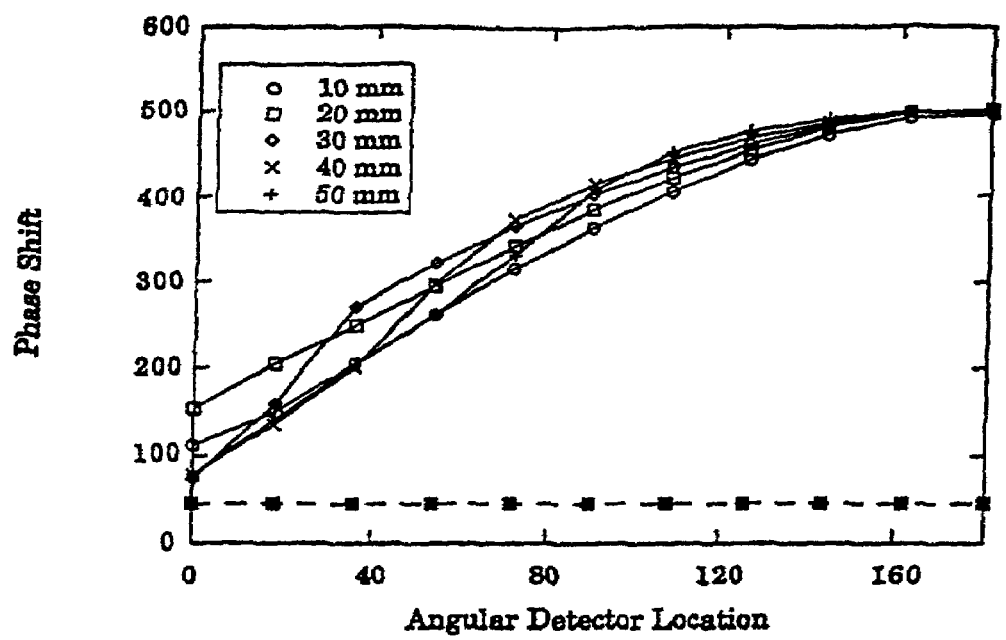
FIG. 17A is a graph of simulated measurements of phase-shift (vertical axis) as a function of angular detector position (horizontal axis) to compare a contrast agent with a 1 nanosecond (ns) lifetime (solid line with open symbols) to a contrast agent with a 1 millisecond (ms) lifetime (dashed line with closed symbols); where the contrast agents are selective to a heterogeneity and the different line styles each correspond 10 millimeter (mm), 20 mm, 30 mm, 40 mm, and 50 mm positions of the heterogeneity.
Figure 17B:
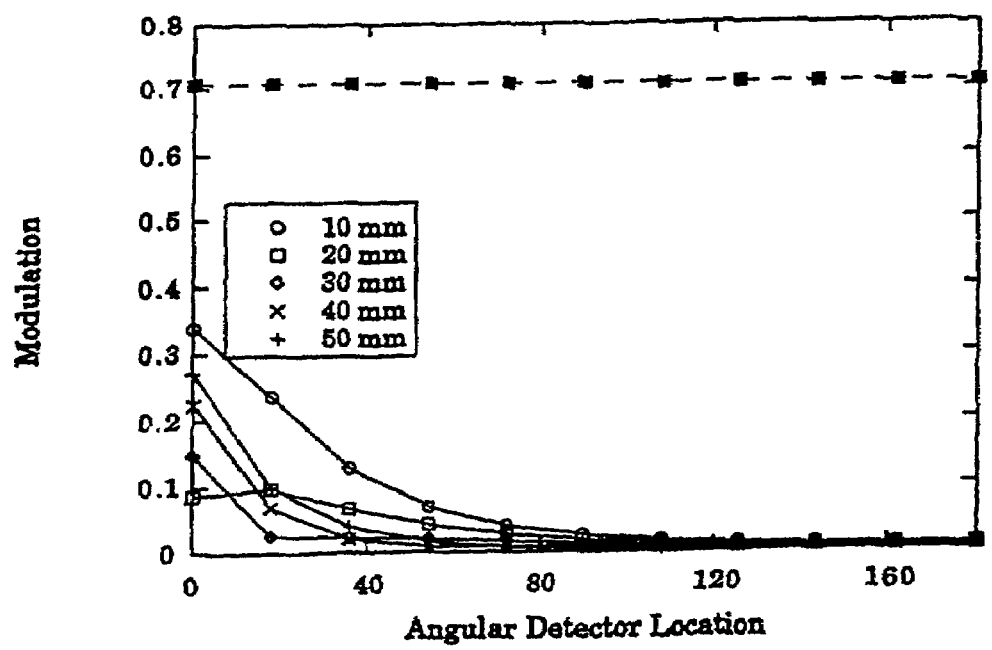
FIG. 17B is a graph of simulated measurements of modulation amplitude (vertical axis) as a function of angular detector position (horizontal axis) to compare a contrast agent with a 1 ns lifetime (solid line with open symbols) to a contrast agent with a 1 ms lifetime (dashed line with closed symbols); where the contrast agents are selective to a heterogeneity and the different line styles each correspond 10 mm, 20 mm, 30 mm, 40 mm, and 50 mm positions of the heterogeneity.

Example 4 demonstrates the unexpected advantage of utilizing a fluorescent contrast agent with a fluorescence lifetime within an order of magnitude of the mean time-of-flight of the interrogating photons. This example compares by computational simulation, the contrast offered by a phosphorescent agent with a lifetime of about 1 millisecond to a fluorescent agent with a lifetime of about 1 nanosecond. Referring to FIG. 16, this simulation assumes a circular tissue phantom 500 with an embedded heterogeneity 502. A single source S1 is indicated and detectors D1 through D11 are spaced about half way around the circular periphery at generally equal intervals. For this comparison $\omega\tau=1$ for both the heterogeneity its surroundings. An uptake of the heterogeneity of 100 times the surroundings (background) was assumed with a corresponding absorption coefficient of fluorophores in the heterogeneity set to 0.1 cm$^{-1}$ versus 0.001 cm$^{-1}$ for the surroundings. The absorption coefficient for nonfluorescing chromophores was set to 0.001 cm$^{-1}$ for both the heterogeneity and surroundings. The graph of FIGS. 17A plots measurements of phase shift (vertical axis) versus angular detector location about the circumference of the tissue phantom 500 (horizontal axis). The lines with open symbols show phase shift variation of a contrast agent with a lifetime of 1 ns with the detector position and changes in location of a heterogeneity containing the contrast agent (different open symbol shapes). The closed symbols correspond to phase shift versus detector position for a contrast agent in the heterogeneity having a lifetime of 1 ms. The graph of FIG. 17B compares these contrast agents in terms of Modulation (vertical axis) versus angular detector location (horizontal axis) and location of the agent-containing heterogeneity (different open symbol shapes). These illustrations indicate that as the lifetime increases, sensitivity of the contrast agent to spatial differences is reduced, and further point to the development of fluorescent contrast agents with intrinsic relaxation kinetics (as characterized by fluorescence lifetime) within an order of magnitude of the photon migration times (i.e. times-of-flight) for imaging based on the behavior of multiply scattered light.

Figure 18A:
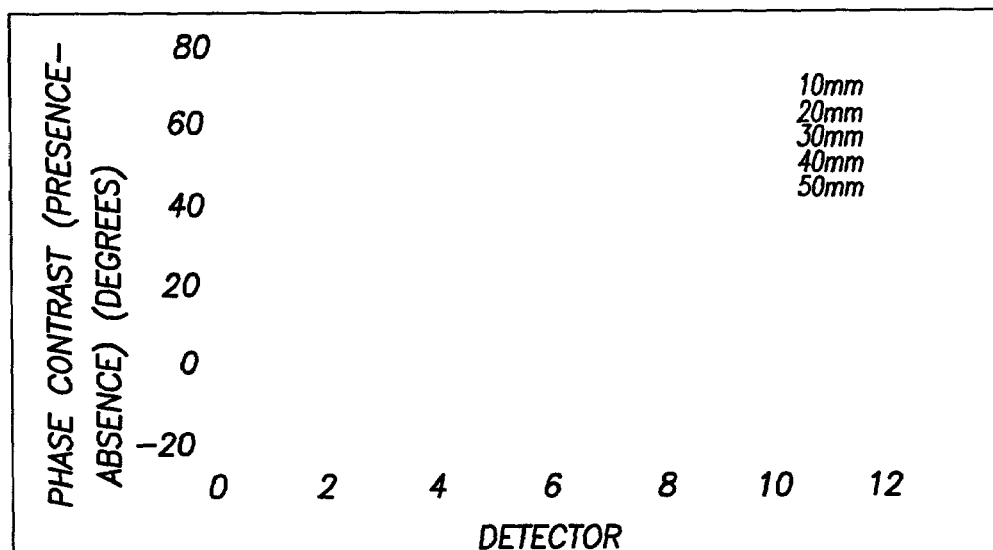
FIG. 18A is a graph of simulated measurements of phase contrast (vertical axis) as a function of detector position (horizontal axis) and location of a heterogeneity (different line styles corresponding to 10 mm, 20 mm, 30 mm, 40 mm, and 50 mm positions); where the heterogeneity contains a light-emitting contrast agent having an uptake into the heterogeneity of 100:1 and a lifetime of 1 ns.
Figure 18B:
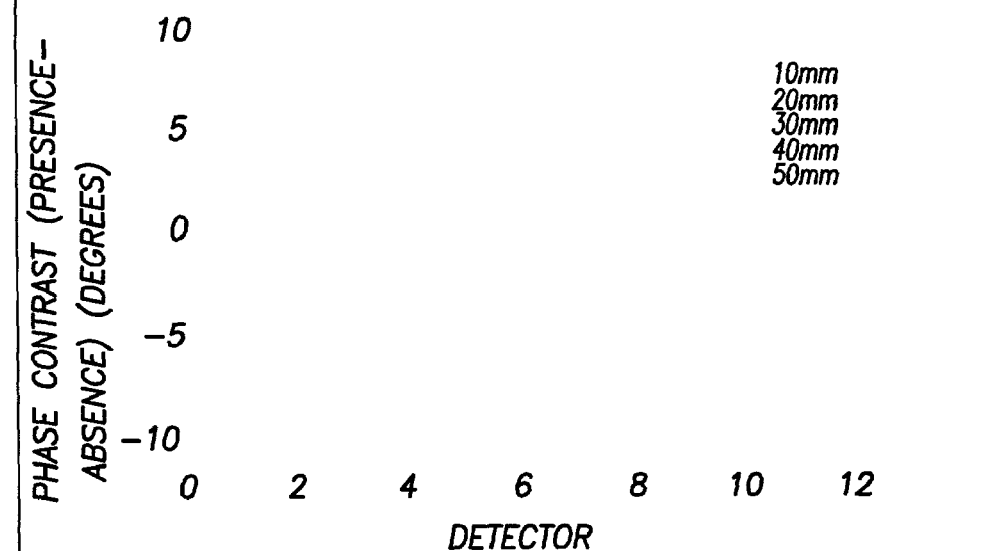
FIG. 18B is a graph of simulated measurements of phase contrast (vertical axis) as a function of detector position (horizontal axis) and location of a heterogeneity (different line styles corresponding to 10 mm, 20 mm, 30 mm, 40 mm, and 50 mm positions); where the heterogeneity contains a light-emitting contrast agent having an uptake into the heterogeneity of 100:1 and a lifetime of 1 ms.
Figure 18C:
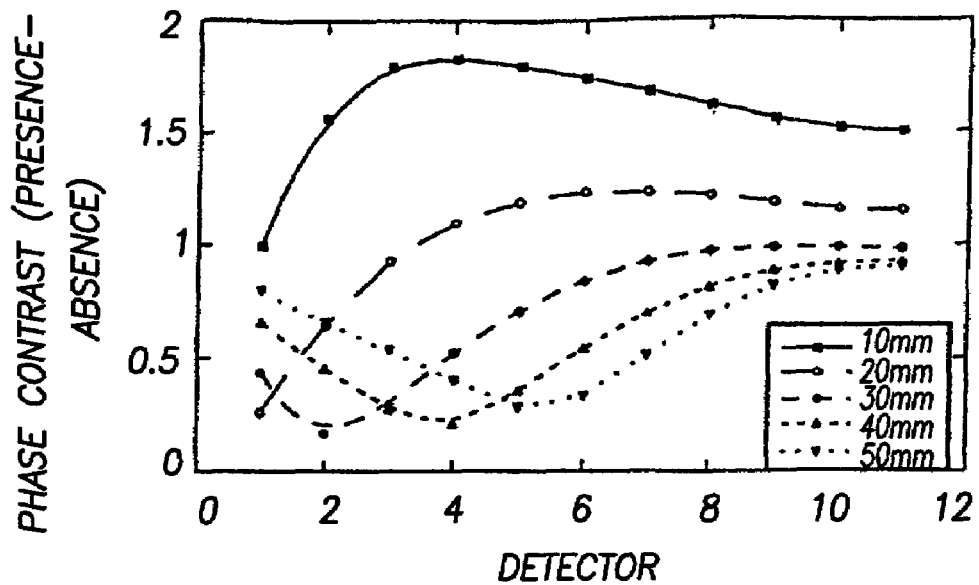
FIG. 18C is a graph of simulated measurements of modulation contrast (vertical axis) as a function of detector position (horizontal axis) and location of a heterogeneity (different line styles corresponding to 10 mm, 20 mm, 30 mm, 40 mm, and 50 mm positions); where the heterogeneity contains a light-emitting contrast agent having an uptake into the heterogeneity of 100:1 and a lifetime of 1 ns.
Figure 18D:
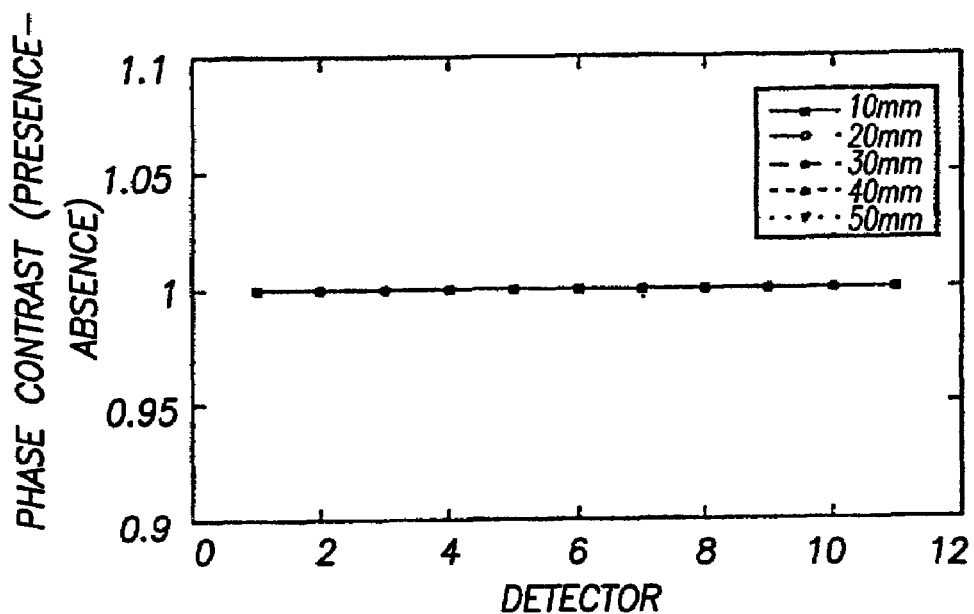
FIG. 18D is a graph of simulated measurements of modulation contrast (vertical axis) as a function of detector position (horizontal axis) and location of a heterogeneity (different line styles corresponding to 10 mm, 20 mm, 30 mm, 40 mm, and 50 mm positions); where the heterogeneity contains a light-emitting contrast agent having an uptake into the heterogeneity of 100:1 and a lifetime of 1 ms.

FIGS. 18A and 18B are calculated simulations using the same phantom tissue and parameters, comparing lifetimes of 1 ns and 1 ms, respectively, as a function of position of the detectors and location of a heterogeneity selective to the corresponding contrast agent. The vertical axis of FIGS. 18A and 18B represents phase contrast $\Delta\theta$. Phase contrast $\Delta\theta$ is the difference between the phase shift in the presence of the heterogeneity and the phase shift in the absence of the heterogeneity, ($\Delta\theta=\theta_{presence}-\theta_{absence}$). FIGS. 18C and 18D are calculated simulations using the same phantom tissue and parameters as FIGS. 18A and 18B to compare the same contrast agent lifetimes in terms of modulation contrast, $\Delta M$ (vertical axis). Modulation contrast $\Delta M$ is provided as the ratio of the modulation ratio (AC/DC) of the detected light in the presence of the heterogeneity to the modulation ratio (AC/DC) of the detected light in the absence of the heterogeneity, ($\Delta M=M_{presence}/M_{absence}$). For all of FIGS. 18A-18D, the horizontal axis corresponds to the detector number and the different line styles correspond to different positions of the contrast agent-bearing heterogeneity.

EXAMPLE 5

The conclusions of the simulation of Example 4 have further been empirically demonstrated by the experimentation of Example 5. The experimental equipment set-up for Example 5 is comparable to system 110. A tissue phantom is prepared by filling a cylindrical Plexiglas container having a 20 cm diameter and a 30.5 cm height with a 0.5% Intralipid solution (supplied by Kabi Parmacia, Clayton, N.C.). A heterogeneity is provided by placing a cylindrical glass container with a 9 mm inner diameter in the Plexiglas container and filling the glass cylinder with the intralipid solution and a contrast agent. The position of the heterogeneity within the Plexiglas container is adjusted with an x-y translation stage model number PMC200-P supplied by Newport of Irvine, Calif.

Figure 19A:
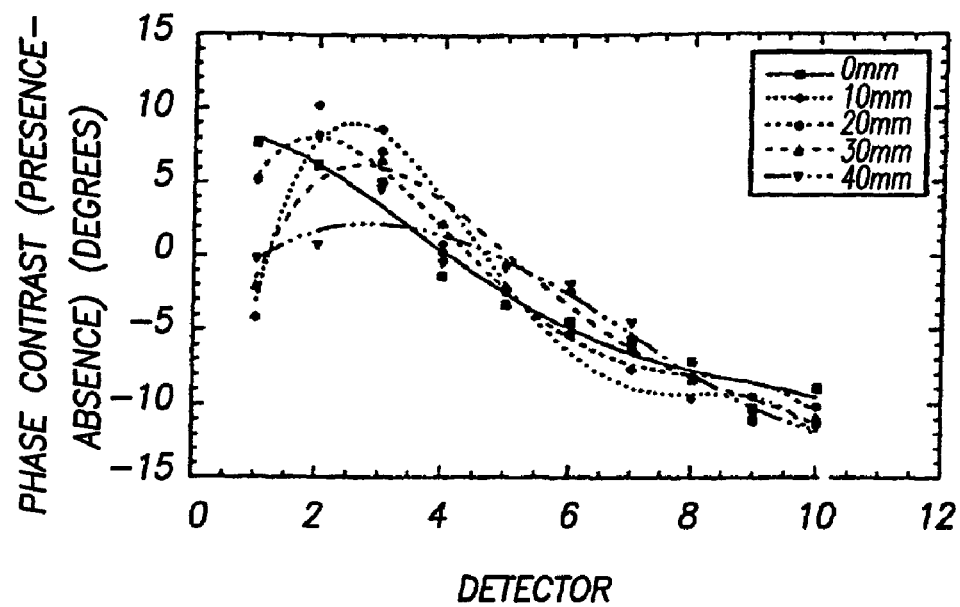
FIG. 19A is a graph of experimental measurements of phase contrast (vertical axis) of emission light as a function of detector position (horizontal axis) and heterogeneity location (different line styles corresponding to 10 mm, 20 mm, 30 mm, and 40 mm) for a 100:1 uptake of an ICG contrast agent into the heterogeneity.
Figure 19B:
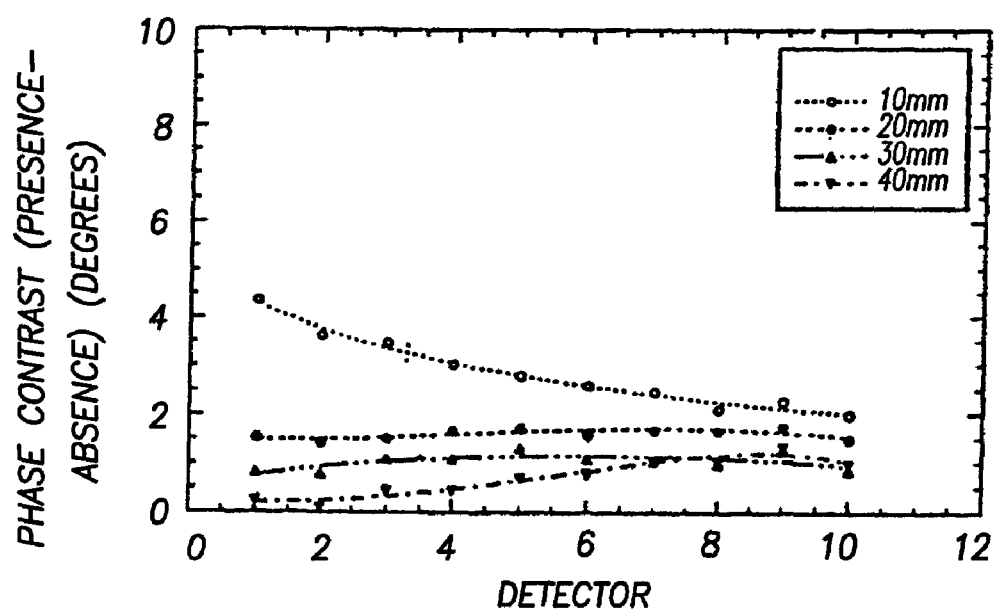
FIG. 19B is a graph of experimental measurements of phase contrast (vertical axis) of emission light as a function of detector position (horizontal axis) and heterogeneity location (different line styles corresponding to 10 mm, 20 mm, 30 mm, and 40 mm) for a 100:1 uptake of an Ru(bpy)$_3^{2+}$ contrast agent into the heterogeneity.

Example 5 experimentally confirms the phase contrast simulated in Example 4 by comparing phase contrast $\Delta\theta$ with a $Ru(bpy)_3^{2+}$ phosphorescent contrast agent in the inner glass container (FIG. 19B) to a fluorescent contrast agent, Indocyanine Green (ICG) (supplied by ACROS Organics, Fairlawn, N.J.), in the inner glass container (FIG. 19A). The contrast agents where added to the intralipid solution in the inner glass container (the "heterogeneity") to simulate a 100:1 uptake ratio. $Ru(bpy)_3^{2+}$ has a lifetime on the order of microseconds. ICG has a lifetime of about 0.58 ns. Notably, by comparing FIGS. 19A and 19B, the phase contrast (vertical axis) provided by a fluorescent agent with its smaller lifetime, is substantially greater than the phase contrast provided by the longer-lived phosphorescent agent $Ru(bpy)_3^{2+}$ as a function of detector number (horizontal axis) and heterogeneity location (different line styles).

EXAMPLE 6

The experimental equipment set-up for Example 6 is comparable to Example 5, except a single source and a single detection point were utilized. The source and detector were placed along the circumference a few degrees apart and the inner container was generally positioned along the midline defined between the source and detector. The x-y stage was used to adjust the position of the inner container along this midline to observe corresponding changes in phase shift $\theta$ and amplitude.

In Example 6, the response of two different fluorescent contrast agents ICG and 3-3'-Diethylthiatricarbocyanine Iodide (designated "DTTCI" herein and supplied by ACROS Organics, Fairlawn, N.J.) to an intensity-modulated excitation light having a wavelength of about 780 nm was detected. The excitation light was modulated at 80 MHz and 160 MHz in different trials corresponding to lines with different symbol shapes. ICG is an agent approved for hepatic and retinal diagnostic testing with a measured lifetime of about 0.58 nanoseconds and DTTCI is a common laser dye with lifetime of about 1.18 nanosecond.

Figure 20A:
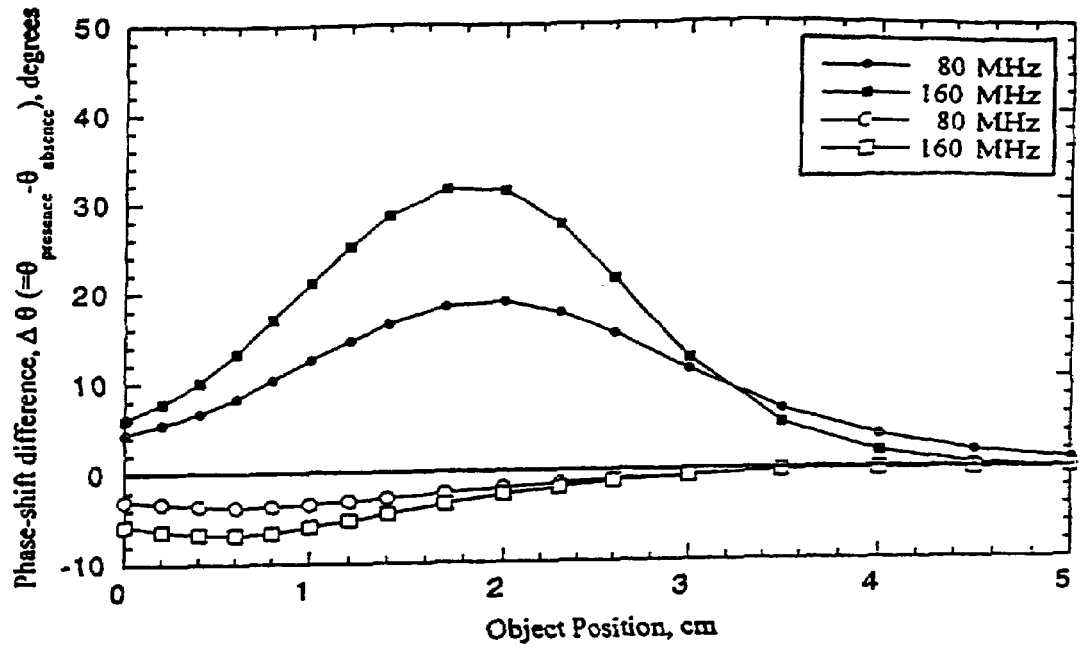
FIG. 20A is a graph comparing absorption measurements (open symbols) and fluorescent measurements (closed symbols) in terms of phase contrast (vertical axis) versus heterogeneity (object) position in centimeters (cm) (horizontal axis) for an ICG contrast agent at modulation frequencies of 80 and 160 megahertz (MHz) (different symbol shapes).
Figure 20B:
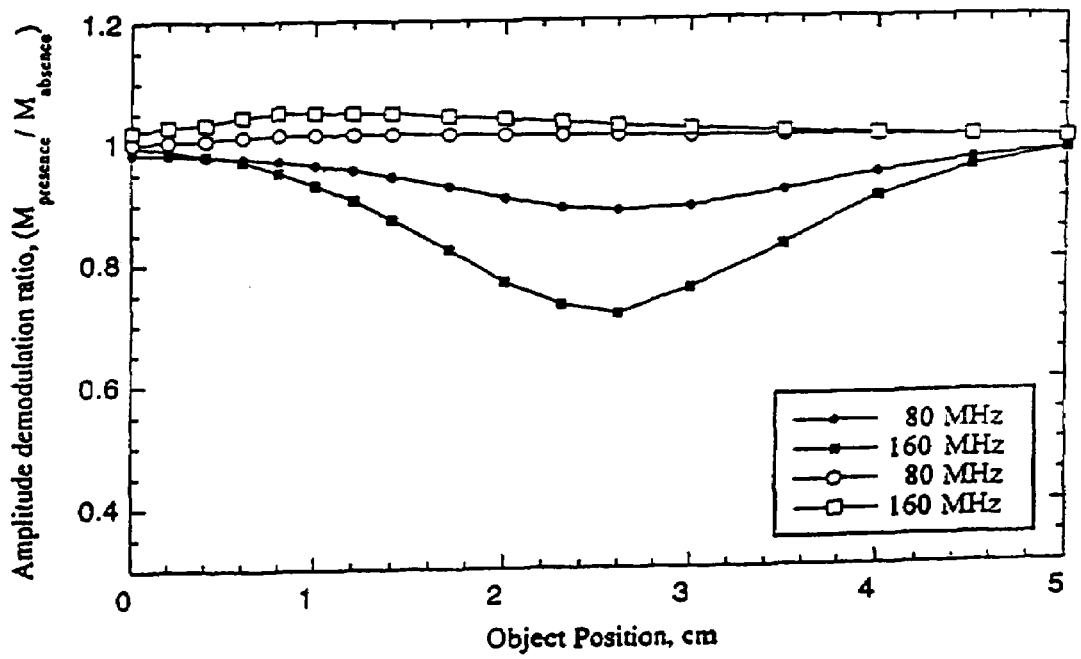
FIG. 20B is a graph comparing absorption measurements (open symbols) and fluorescent measurements (closed symbols) in terms of modulation contrast (vertical axis) versus heterogeneity position (horizontal axis) for an ICG contrast agent at modulation frequencies of 80 and 160 megahertz (MHz) (different symbol shapes).

The phase shift and modulation ratio of the tissue phantom in the absence of the heterogeneity was measured to provide the "absence" case needed to calculate phase contrast $\Delta\theta$ and modulation contrast $\Delta M$. Next, an ICG contrast agent was prepared by adding about a 2.0 µmole ICG concentration to a 0.5% intralipid solution in the inner container. The ICG sample was then exposed to excitation light from the source and the response detected. This detection included measurement of absorption at a wavelength of 780 nm and fluorescence at 830 nm. The resulting phase contrast $\Delta\theta$ at the absorption wavelength (open symbols) and for fluorescence wavelength (closed symbols) for the ICG sample was plotted on the vertical axis of the graph provided in FIG. 20A with the horizontal axis showing the relative position of the heterogeneity ("object") in centimeters as it is moved toward the detector and source along the midline. The resulting modulation contrast $\Delta M$ at the absorption wavelength (open symbols) and at fluorescence wavelength (closed symbols) for the ICG sample was plotted on the vertical axis of the graph provided by FIG. 20B with the horizontal axis showing the relative position of the object in centimeters as it is moved toward the detector and source along the midline.

Figure 20C:
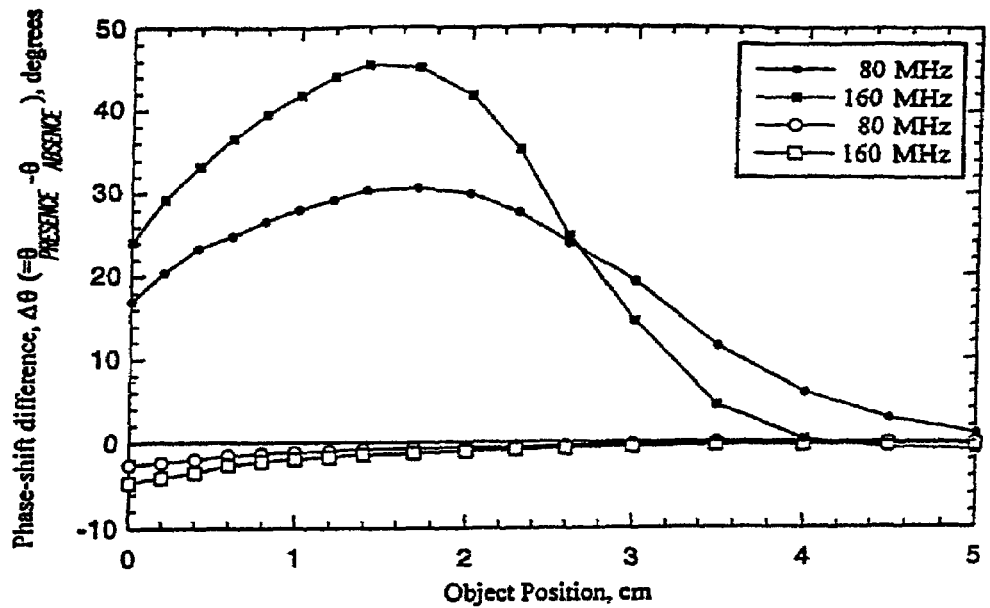
FIG. 20C is a graph comparing absorption measurements (open symbols) and fluorescent measurements (closed symbols) in terms of phase contrast (vertical axis) versus heterogeneity position (horizontal axis) for an DTTCI contrast agent at modulation frequencies of 80 and 160 megahertz (MHz) (different symbol shapes).
Figure 20D:
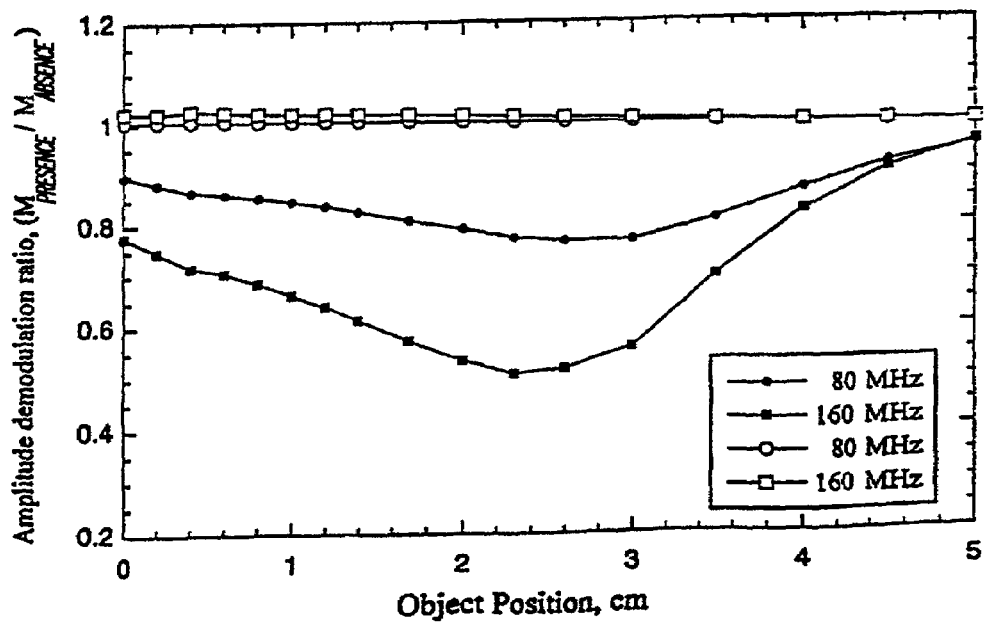
FIG. 20D is a graph comparing absorption measurements (open symbols) and fluorescent measurements (closed symbols) in terms of modulation contrast (vertical axis) versus heterogeneity position (horizontal axis) for an DTTCI contrast agent at modulation frequencies of 80 and 160 megahertz (MHz) (different symbol shapes).
Figure 21A:
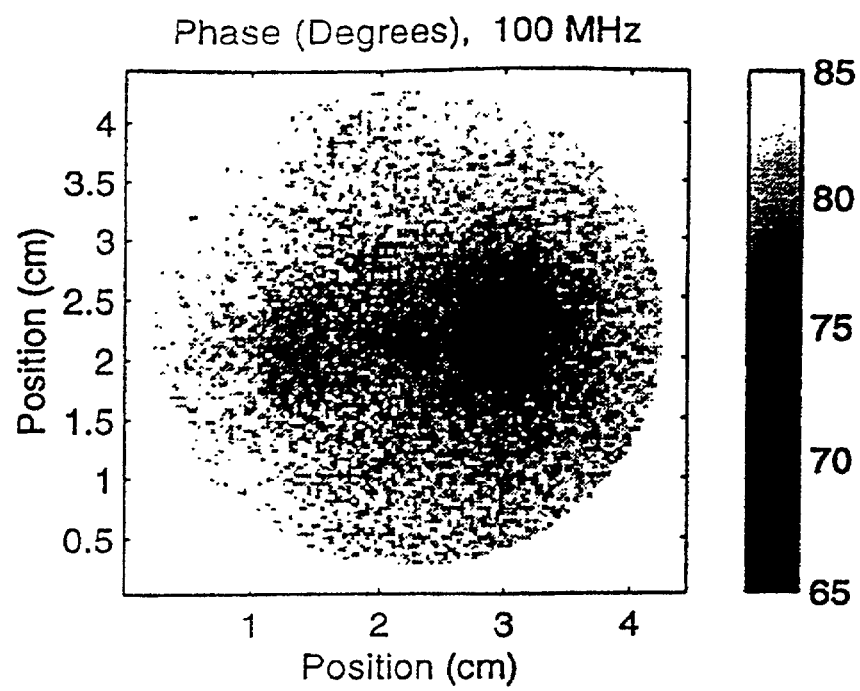
FIGS. 21A-21D are computer-generated gray scale images formed from experimental measurements depicting spatial variation for a tissue phantom including separated ICG and DTTCI heterogeneities in terms of modulation phase-shift, AC modulation amplitude, average DC intensity, and modulation ratio (AC/DC), respectively.
Figure 21B:
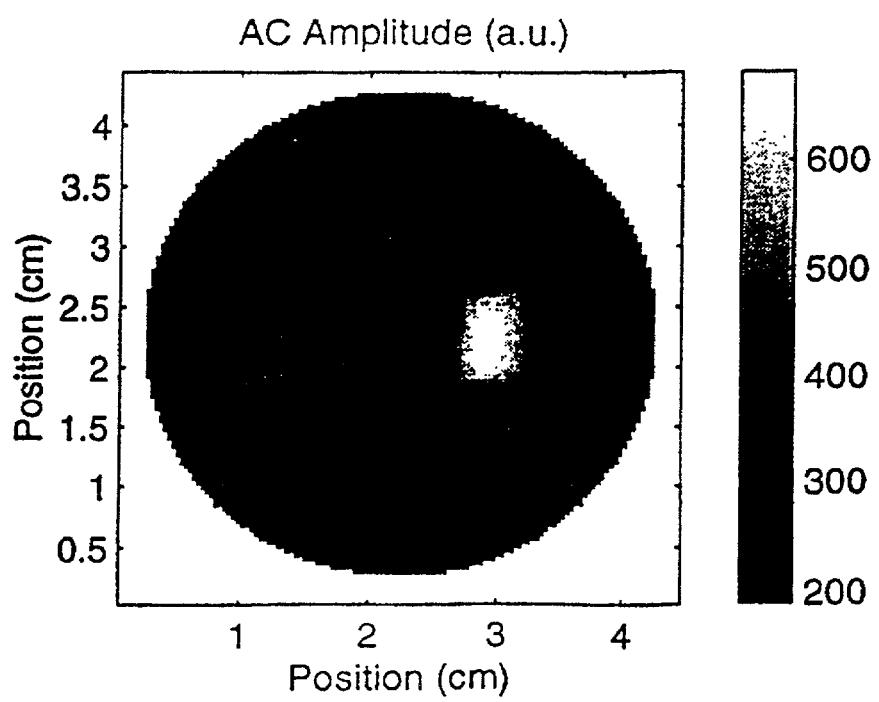
Figure 21C:
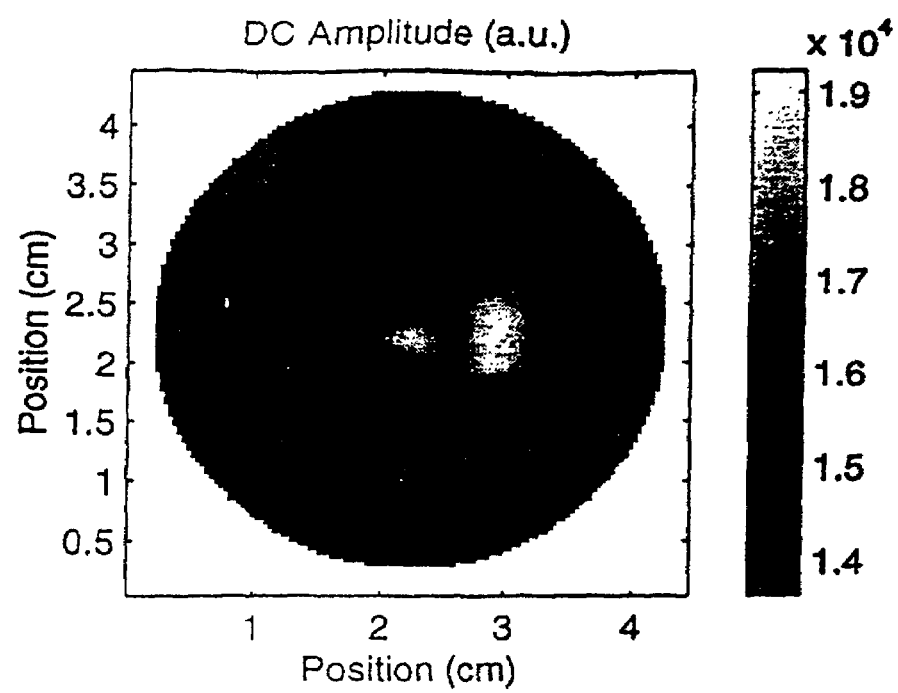
Figure 21D:
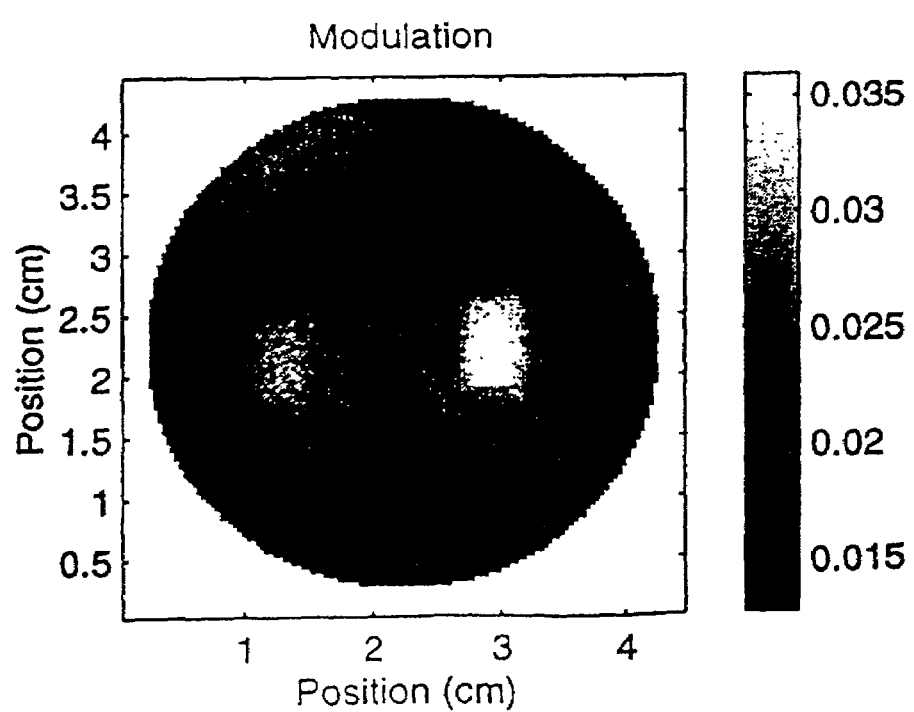
Figure 22A:
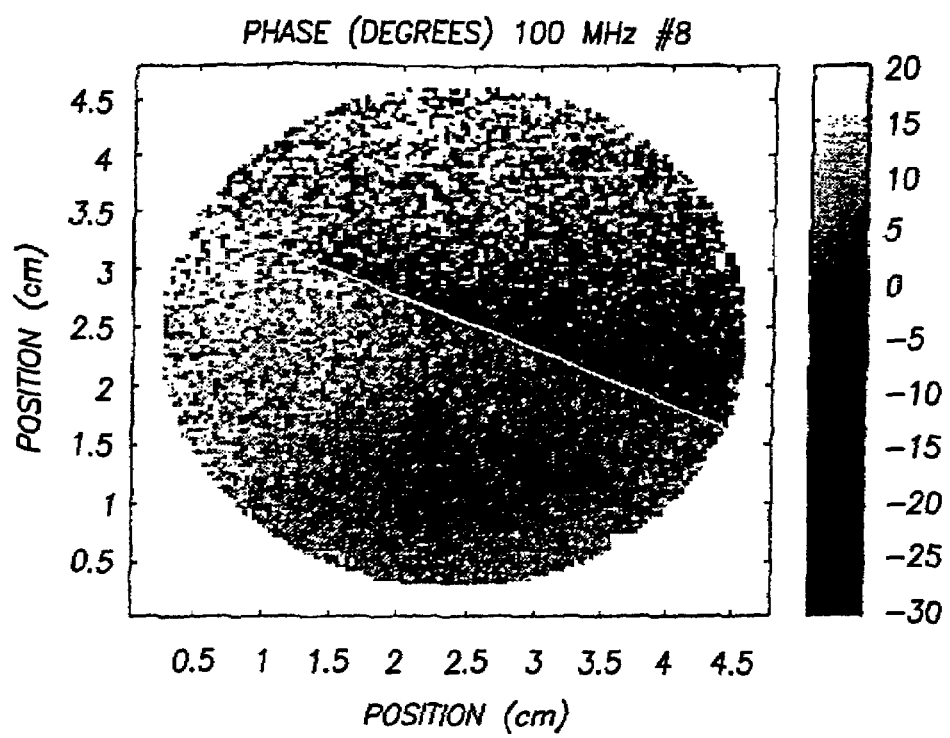
Figure 22B:
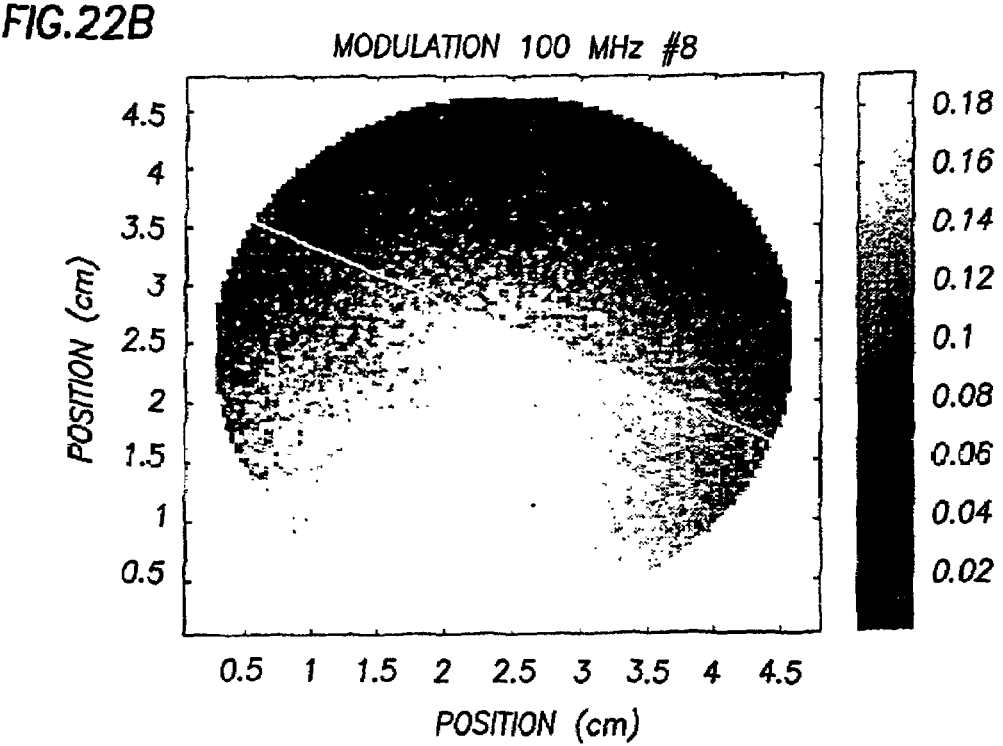

After ICG sample was tested, a 4.2 µmole concentration of the DTTCI contrast agent was added to the 0.5% intralipid solution in the inner container to provide a DTTCI sample. The different concentration of the ICG and DTTCI contrast agents were selected to provide a fluorescent cross-section that is generally the same for both the ICG and DTTCI samples. The resulting phase contrast $\Delta\theta$ at the absorption wavelength (open symbols) and at the fluorescence wavelength (closed symbols) for the DTTCI sample is plotted on the vertical axis of the graph provided in FIG. 20C with the horizontal axis showing the relative position of the object in centimeters as it is moved toward the detector and source along the midline. The resulting modulation contrast $\Delta M$ at the absorption wavelength (open symbols) and for fluorescence wavelength (closed symbols) for the DTTCI sample is plotted on the vertical axis of the graph provided in FIG. 20D with the horizontal axis showing the relative position of the object in centimeters as it is moved toward the detector and source along the midline.

For both samples, the fluorescence decay process is single exponential, showing one lifetime, but the analysis and approach can be extended to dyes and contrast agents with more than one lifetime. Upon comparing the fluorescent phase and amplitude modulation generated by the two fluorescent contrast agents, the impact of fluorescence lifetime $\tau$ over absorption may readily be observed. Indeed, it has been found that substantial contrast is present when the uptake is only 10:1 over the surroundings or background.

EXAMPLE 7

For Example 7, a phantom tissue is prepared by placing a tissue-mimicking Intralipid solution in a Plexiglas container. The excitation light source transilluminates the tissue phantom from the rear along a straight-line distance of about 8 centimeters. An image intensifier/CCD detection arrangement was utilized to detect the response. The experimental set-up for Example 7 was comparable to system 410 illustrated in FIG. 15.

Embedded within the middle of the Plexiglas container tissue phantom were two micromolar intralipid solutions of 0.5 ml in separate containers each having a different fluorescent contrast agent. One vessel included an ICG contrast agent and the other vessel included a DTTCI contrast agent. Measurements of the fluorescent phase-shift, AC amplitude, DC intensity, and modulation (AC/DC) were conducted across the front of the phantom tissue in response to a 100 MHz modulated excitation light at 780 nm. FIGS. 21A-21D are two-dimensional images depicting the spatial variation of the phase-shift, AC amplitude, DC intensity, and modulation measurements; respectively, in terms of a corresponding gray scale. These images confirm the variation in contrast with differences in fluorescence lifetime and the parameter being measured.

EXAMPLE 8

Example 8 is a live tissue study of mammary tissue from a dog, Sugar Limburg, which was a miniature poodle (age 10 years and weight 12.5 lbs.). An in vivo image of the right fifth mammary glad was taken after an in vivo injection with 1.3 cc of a 5% concentration of ICG fluorescent contrast agent. Interrogation was performed with an experimental set-up comparable to Example 7, with an excitation light wavelength of 789 nm and detection at a 830 nm wavelength. The modulation frequency was 100 MHz.

A frozen section of the right fifth mammary revealed two dark spots approximately 1 cm deep from the tissue surface which were histologically classified as reactive regional inguinal lymph nodes with no evidence of metastatic spread. The remaining tissue was classified as lobular hyperplasia with no evidence of tumor. FIGS. 22A-22D are 2-dimensional images depicting spatial variation in terms of in vivo measurement from the emission light for modulation phase, modulation ratio, average intensity, and modulation amplitude, respectively, relative to corresponding gray scales. The white line in the image of FIGS. 22A-22D is the air-tissue boundary. The phase shift in the tissue is small due to the small amount of mammary tissue present. Also, the modulation ratio contains a large amount of background noise. However, the two light spots at the bottom of both the average intensity and the modulation amplitude are believed to correspond to an increased uptake of ICG inside the enlarged lymphatic tissue.

All publications and patent applications cited in this specification are herein incorporated by reference as if each individual publication or patent application were specifically and individually indicated to be incorporated by reference; including U.S. Patent Application Ser. Nos. 60/039,318 filed 7 Feb. 1997 and Ser. No. 08/702,060 filed 23 Aug. 1996. While the invention has been illustrated and described in detail in the drawings and foregoing description, the same is to be considered as illustrative and not restrictive in character, it being understood that only the preferred embodiments have been shown and that all modifications that come within the spirit of the invention are desired to be protected.

What is claimed is:

1. A method, comprising:
    introducing an exogenous fluorescent contrast agent into a biologic tissue, the tissue multiply scattering light with a mean time-of-flight, and the agent having a fluorescence lifetime within a factor of about ten of the mean time-of-flight;
    exposing the tissue to an excitation light with a predetermined time-varying intensity;
    detecting a light emission from the tissue in response to said exposing;
    generating an image of the tissue by mapping spatial variation of a level of a fluorescence characteristic of the tissue from the light emission in accordance with a mathematical expression modeling multiple light scattering behavior of the tissue; and
    wherein the agent is selected in accordance with a predetermined relationship between degree of image contrast and at least one of fluorescence yield or the fluorescence lifetime.

2. The method of claim 1, wherein the at least one is fluorescence lifetime.

3. The method of claim 1, wherein the fluorescence lifetime is in a range of about 0.1 to 10 nanoseconds.

4. The method of claim 1, wherein the fluorescence lifetime is in a range of about 0.5 to 5 nanoseconds.

5. The method of claim 1, wherein the fluorescence lifetime is in a range of about 0.2 to 2 nanoseconds.

6. The method of claim 1, wherein the mathematical expression corresponds to a diffusion equation approximation of multiply scattered light.

7. The method of claim 1, wherein the fluorescence characteristic is at least one of fluorescence lifetime, fluorescence yield, or fluorescence quantum efficiency.

8. The method of claim 1, wherein said generating includes determining a modulation amplitude change and a phase change of the light emission relative to the excitation light.

9. The method of claim 8, wherein the fluorescence characteristic corresponds to the fluorescence lifetime.

10. The method of claim 9, wherein the mathematical expression is in a frequency domain form and the image contrast is provided in terms of at least one of phase shift contrast or modulation contrast.

11. A method comprising:
    selecting a fluorescent contrast agent as a function of a predetermined time-of-flight for a tissue to be imaged in accordance with a mathematical expression modeling the behavior of multiply scattered light traveling through the tissue, the fluorescent contrast agent having a fluorescence lifetime within a factor of ten of the predetermined time-of-flight; and
    providing the fluorescent agent for introduction into the tissue.

12. The method of claim 11, wherein the fluorescence lifetime is in a range of about 0.1 to 10 nanoseconds.

13. The method of claim 11, wherein the fluorescence lifetime is in a range of about 0.5 to 5 nanoseconds.

14. The method of claim 11, wherein the fluorescence lifetime is in a range of about 0.2 to 2 nanoseconds.

15. The method of claim 11, wherein the mathematical expression corresponds to a diffusion equation approximation of multiply scattered light.

16. The method of claim 11, further comprising generating an image of the tissue by mapping spatial variation of a level of a fluorescence characteristic of the tissue.

* * * * *